(12) United States Patent
Oh et al.

(10) Patent No.: US 12,227,510 B2
(45) Date of Patent: Feb. 18, 2025

(54) CRYSTAL FORM OF ACID ADDITION SALT OF FUROPYRIMIDINE COMPOUND

(71) Applicant: HANMI PHARM. CO., LTD., Hwaseong-si (KR)

(72) Inventors: Hee Sook Oh, Hwaseong-si (KR); Jae Hyuk Jung, Hwaseong-si (KR); Ji Young Jeon, Hwaseong-si (KR); Sun Young Jang, Hwaseong-si (KR); Tae Hee Ha, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 759 days.

(21) Appl. No.: 17/599,044

(22) PCT Filed: Mar. 20, 2020

(86) PCT No.: PCT/KR2020/003850
§ 371 (c)(1),
(2) Date: Sep. 28, 2021

(87) PCT Pub. No.: WO2020/204426
PCT Pub. Date: Oct. 8, 2020

(65) Prior Publication Data
US 2022/0177483 A1   Jun. 9, 2022

(30) Foreign Application Priority Data
Mar. 29, 2019   (KR) .................. 10-2019-0037060

(51) Int. Cl.
C07D 491/04   (2006.01)

(52) U.S. Cl.
CPC ........ C07D 491/04 (2013.01); C07B 2200/13 (2013.01)

(58) Field of Classification Search
CPC   C07D 491/04; C07B 2300/13; A61K 31/519; A61P 35/00; A61P 19/02
See application file for complete search history.

(56) References Cited

U.S. PATENT DOCUMENTS

| 8,314,109 B2 | 11/2012 | Peyronel |
| 9,012,464 B2 | 4/2015 | Gidwani et al. |
| RE46,511 E | 8/2017 | Cha et al. |
| 10,464,946 B2 | 11/2019 | Jung et al. |
| 10,596,183 B2 | 3/2020 | He |
| 11,008,333 B2 | 5/2021 | Baek et al. |
| 2019/0388410 A1 | 12/2019 | Bothe et al. |

FOREIGN PATENT DOCUMENTS

| CN | 103476770 A | 12/2013 | | |
| CN | 105061438 A | 11/2015 | | |
| EA | 022749 B1 | 2/2016 | | |
| KR | 10-2005-0091462 A | 9/2005 | | |
| KR | 10-2010-0109940 A | 10/2010 | | |
| KR | 10-1589114 B1 | 1/2016 | | |
| KR | 10-2018-0089903 A | 8/2018 | | |
| KR | 10-2018-0089904 A | 8/2018 | | |
| RU | 2 523 279 C2 | 7/2014 | | |
| WO | 2005/092896 A1 | 10/2005 | | |
| WO | 2008/015005 A2 | 2/2008 | | |
| WO | WO-2008054827 A2 * | 5/2008 | ........... | C07D 487/04 |
| WO | 2010/126138 A1 | 11/2010 | | |
| WO | WO-2011162515 A2 * | 12/2011 | ........... | A61K 31/519 |
| WO | 2016/174183 A1 | 11/2016 | | |
| WO | WO-2017116192 A1 * | 7/2017 | ........... | A61K 31/496 |
| WO | 2017/218844 A2 | 12/2017 | | |

OTHER PUBLICATIONS

Bhaskaran (Toxicologic Pathology vol. 46 pp. 460-472 published online Jun. 2018) (Year: 2018).*
Indian Office Action dated Feb. 15, 2023 in Indian Application No. 202117046895.
Caira, "Crystalline Polymorphism of Organic Compounds", Topics in Current Chemistry, Springer, Jan. 1998, vol. 198, pp. 163-208 (46 pages total).
International Search Report for PCT/KR2020/003850 dated Jun. 18, 2020 (PCT/ISA/210).
Richard J. Bastin, et al., "Salt Selection and Optimisation Procedures for Pharmaceutical New Chemical Entities", Organic Process Research & Development, 2000, vol. 4, p. 427-435.
Sherry L. Morissette, et al., "High-throughput crystallization: polymorphs, salts, co-crystals and solvates of pharmaceutical solids", Advanced Drug Delivery Reviews, 2004, v.56, pp. 275-300 (Sections 1; 3.1).
Communication dated Apr. 27, 2023 in Russian patent Application No. 2021129799.
Search Report dated Apr. 27, 2023 in Russian patent Application No. 2021129799.
Luigh et al, "Crystalline Drugs", People Health Press, 1st Edition, Oct. 2009, pp. 5-13 (11 pages).
Chinese Office Action dated Nov. 24, 2023 in Application No. 202080025968.3.
Evan a Thackaberry, "Non-clinical toxicological considerations for pharmaceutical salt selection" Expert Opinion on Drug Metabolism & Toxicology, 2012, vol. 8, No. 11, pp. 1419-1433 (16 pages total).
Fang Tian, et al., "Factors affecting crystallization of hydrates", JPP, 2010, vol. 62, pp. 1534-1546 (13 pages).
C.G.Wermuth Knitting, vol. 1999, Technobiology, 1999, pp. 347 to 365 (20 pages total).
Hirayama Yoshinaki, organic compound crystal production handbook, 2008, pp. 17 to 23, p. 37, and to p. 40, and p. 45, and pp. 51,57, and 65 (28 pages total).
A polymorphism of medicines and crystallization, 2002, pp. 273, 278, and 305 (16 pages total).

(Continued)

Primary Examiner — Theodore R. Howell
Assistant Examiner — George W Kosturko
(74) Attorney, Agent, or Firm — Sughrue Mion, PLLC

(57) ABSTRACT

Provided are crystalline forms of acid addition salts of N-(3-(2-(4-(4-methylpiperazin-1-yl)phenylamino)furo[3,2-d]pyrimidin-4-yloxy)phenyl)acrylamide, and a pharmaceutical composition including the same. The crystalline forms may be easily used in preparing the pharmaceutical composition including the same as an active ingredient.

5 Claims, 18 Drawing Sheets

(56) References Cited

OTHER PUBLICATIONS

Communication dated Nov. 6, 2023 issued in Japanese Application No. 2021-557870.
Office Action issued Jun. 10, 2024 in Israeli Application No. 286692.
"Pharmaceutical Dosage Forms: Tablets", edited by Larry L. Augsburger, et al., 2008, Informa Healthcare USA Inc., 3rd Edition, vol. 2: Rational Design and Formulation (570 pages total).
P. Heinrich Stahl, "Preparation of Water-Soluble Compounds Through Salt Formation", The Practice of Medicinal Chemistry, 2003, pp. 601-615 (15 pages total).
"Polymorphism in pharmaceutical solids", Edited by Harry G. Brittain, Drugs and the Pharmaceutical Sciences, 2009, Informa Healthcare USA Inc., vol. 192 (323 pages total).
Office Action issued Jun. 25, 2024 in Mexican Application No. MX/a/2021/011791.
Stephen M. Berge, et al., "Pharmaceutical Salts", Journal of Pharmaceutical Sciences, Jan. 1977, vol. 66, No. 1, pp. 1-19 (19 pages total).

* cited by examiner

CRYSTAL FORM OF ACID ADDITION SALT OF FUROPYRIMIDINE COMPOUND

CROSS REFERENCE TO RELATED APPLICATIONS

This application is a National Stage of International Application No. PCT/KR2020/003850 filed Mar. 20, 2020, claiming priority based on Korean Patent Application No. 10-2019-0037060 filed Mar. 29, 2019.

TECHNICAL FIELD

The present disclosure relates to crystalline forms of acid addition salts of a furopyrimidine compound represented by the following Formula 1, which has a tyrosine kinase activity-inhibitory effect and is useful in treating cancer and autoimmune diseases such as rheumatoid arthritis, and a pharmaceutical composition including the same. More particularly, the present disclosure relates to crystalline forms of acid addition salts of N-(3-(2-(4-(4-methylpiperazin-1-yl)phenylamino)furo[3,2-d]pyrimidin-4-yloxy)phenyl)acrylamide, and a pharmaceutical composition including the same.

[Formula 1]

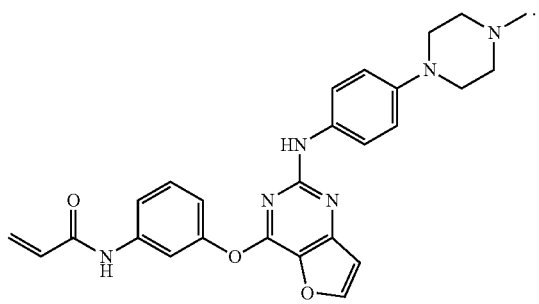

BACKGROUND ART

A compound of the following Formula 1 which has a chemical name of N-(3-(2-(4-(4-methylpiperazin-1-yl)phenylamino)furo[3,2-d]pyrimidin-4-yloxy)phenyl)acrylamide is disclosed in Korean Patent No. 1,589,114 and International Patent Publication No. 2011162515. The compound has selective inhibitory activity against a variant epithelial growth factor receptor tyrosine kinase, and thus is useful in treating benign or malignant tumors, inflammatory diseases, or autoimmune diseases such as rheumatoid arthritis.

[Formula 1]

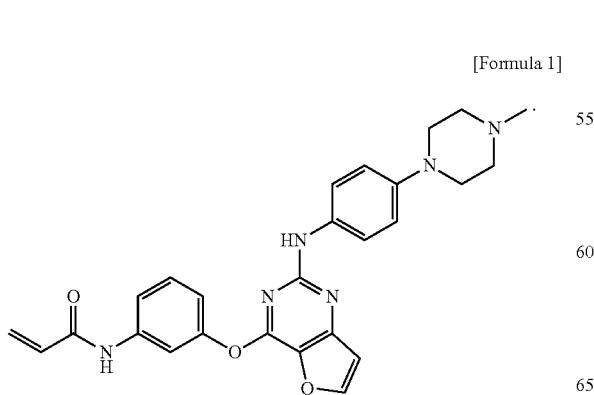

In addition, the reference documents disclose a method of preparing the compound of Formula 1.

However, the compound of Formula 1 prepared in the reference documents is generally prepared as an amorphous solid which is a form less suitable for large-scale production of pharmaceutical drugs. In addition, the compound of Formula 1 as prepared in the above reference documents has a disadvantage in that its solubility in water is very low (less than 0.001 mg/mL).

Therefore, it is necessary to prepare a salt of the compound of Formula 1 in a crystalline form, which satisfies strict requirements for pharmaceutical formulations and specific details thereof while having improved solubility in water.

Accordingly, the present inventors investigated whether acid addition salts of the compound of Formula 1 are produced using various acids and solvents according to different conditions and procedures for the compound of Formula 1. Further, the present inventors evaluated physicochemical properties such as solubility, hygroscopicity, stability, etc. of the acid addition salts. As a result, it was found that crystalline forms of hydrochloride, methanesulfonate, and ethanesulfonate among acid addition salts of the compound of Formula 1 are excellent in terms of overall physicochemical properties pharmaceutically required, such as excellent solubility in water, long-term stability without requiring specific storage conditions, etc., and thus they may be easily used in preparing a pharmaceutical composition including the same as an active ingredient, thereby completing the present disclosure.

DESCRIPTION OF EMBODIMENTS

Technical Problem

Accordingly, an object of the present disclosure is to provide a crystalline form of an acid addition salt, for example, hydrochloride, methanesulfonate, or ethanesulfonate of a furopyrimidine compound of Formula 1, and a pharmaceutical composition including the same.

Solution to Problem

According to the above object, an aspect provides a crystalline form of an acid addition salt of a compound of the following Formula 1:

[Formula 1]

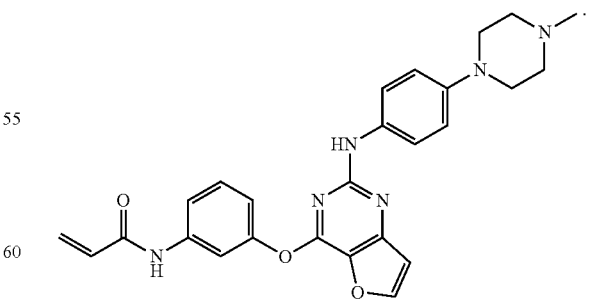

In a specific embodiment, the acid addition salt of the compound of Formula 1 is hydrochloride.

In a specific embodiment, the acid addition salt of the compound of Formula 1 is methanesulfonate.

In a specific embodiment, the acid addition salt of the compound of Formula 1 is ethanesulfonate.

In a specific embodiment, the acid addition salt of the compound of Formula 1 may be one or more selected from the group consisting of hydrochloride, methanesulfonate, and ethanesulfonate.

In a specific embodiment, the acid addition salt of the compound of Formula 1 may be in the form of an anhydride or a hydrate. For example, the acid addition salt of the compound of Formula 1 may be monohydrate, dihydrate, or trihydrate, but is not limited thereto.

Specific examples of the crystalline form are the same as follows:

- a crystalline form of dihydrochloride trihydrate ($2HCl \cdot 3H_2O$) of the compound of Formula 1 having an X-ray powder diffraction (XRPD) spectrum including peaks at diffraction angles ($2\theta \pm 0.2°$) of 6.4°, 7.1°, 12.8°, and 21.2°, when irradiated with a Cu-Kα light source;
- a crystalline form of monohydrochloride dihydrate ($1HCl \cdot 2H_2O$) of the compound of Formula 1 having an XRPD spectrum including peaks at diffraction angles ($2\theta \pm 0.2°$) of 7.0°, 7.9°, 15.8°, 17.2°, 18.6°, 20.6°, 21.3°, and 23.2°, when irradiated with a Cu-Kα light source;
- a crystalline form of monohydrochloride anhydrous (1HCl) of the compound of Formula 1 having an XRPD spectrum including peaks at diffraction angles ($2\theta \pm 0.2°$) of 4.9°, 14.8°, and 21.2°, when irradiated with a Cu-Kα light source.
- a crystalline form of methanesulfonic anhydride (1MsOH) of the compound of Formula 1 having an XRPD spectrum including peaks at diffraction angles ($2\theta \pm 0.2°$) of 11.8°, 17.2°, 19.0°, 20.0°, 22.8°, and 24.0°, when irradiated with a Cu-Kα light source;
- a crystalline form of methanesulfonate monohydrate ($1MsOH \cdot 1H_2O$) of the compound of Formula 1 having an XRPD spectrum including peaks at diffraction angles ($2\theta \pm 0.2°$) of 7.6°, 15.2°, 17.0°, 18.7°, 20.8°, and 22.8°, when irradiated with a Cu-Kα light source; and
- a crystalline form of ethanesulfonic anhydride (1 EsOH) of the compound of Formula 1 having an XRPD spectrum including peaks at diffraction angles ($2\theta \pm 0.2°$) of 17.1°, 18.6°, 21.3°, 22.3°, 23.0°, and 23.6°, when irradiated with a Cu-Kα light source.

In a specific embodiment, the crystalline forms are in substantially pure forms, respectively.

As used herein, the term "substantially pure" means at least 95% pure, specifically 99% pure, wherein 95% pure means 5% or less, and 99% pure means 1% or less, of any other form of the compound of Formula 1 being present (other crystalline form, amorphous form, etc.).

Another aspect provides a pharmaceutical composition including one or more of the above crystalline forms of the compound of Formula 1 and one or more pharmaceutically acceptable carriers and/or diluents.

The pharmaceutical composition may be used for the treatment of benign or malignant tumors, inflammatory diseases, or autoimmune diseases such as rheumatoid arthritis, which are caused by epithelial growth factor receptor tyrosine kinase or a variant thereof.

Advantageous Effects of Disclosure

A crystalline form of a compound of Formula 1 according to an aspect, e.g., hydrochloride, methanesulfonate, or ethanesulfonate is excellent in terms of overall physicochemical properties, i.e., solubility in water, hygroscopicity, chemical stability, etc., thereby being easily used in a pharmaceutical composition including the same as an active ingredient.

MODE OF DISCLOSURE

Figure 1A:
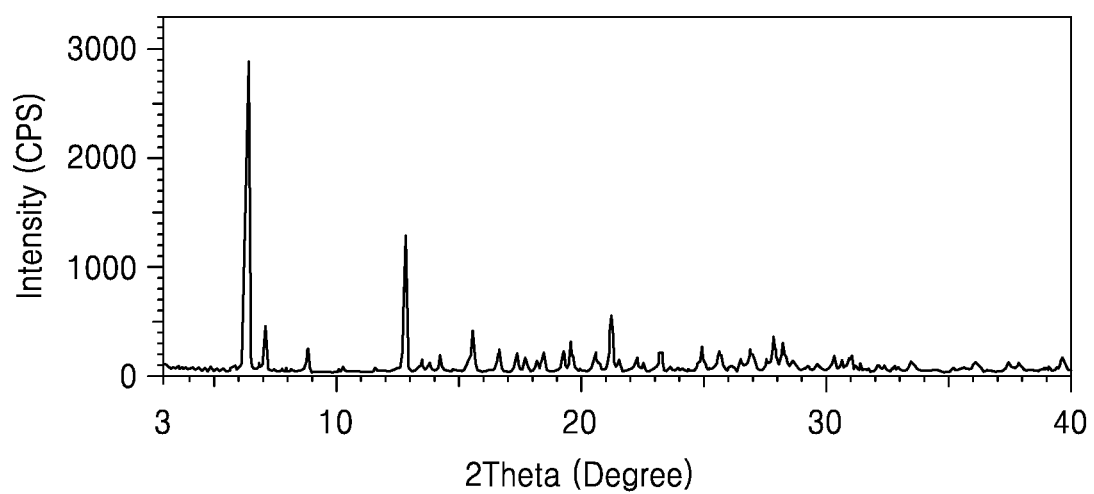
FIGS. 1A to 1F show X-ray powder diffraction (XRPD) spectra of crystalline forms of acid addition salts of a compound of Formula 1 according to exemplary embodiments.

Terms not specifically defined herein are given the meanings that would be given to them by one skilled in the art in light of the disclosure and the context. However, unless otherwise specified, the term described below will have the meaning indicated below over the entire specification:

The term "about" refers to being within 5% of a predetermined value or range, and specifically, within 1% to 2%. For example, "about 10%" refers to 9.5% to 10.5%, and specifically, 9.8% to 10.2%. For another example, "about 100° C." refers to 95° C. to 105° C., and specifically, 98° C. to 102° C.

le;2qUnless otherwise specified, a skilled practitioner will understand that the values of peaks from X-ray powder diffraction studies reported in the present disclosure are associated with experimental errors generally observable in this field. Specifically, a peak is interpreted as to be located within ±0.5° of the value reported herein. More specifically, a peak is interpreted as to be located within ±0.2° of the value reported herein.

The term "acid addition salt" refer to a salt with an inorganic acid or an organic acid capable of forming a salt by acid-base reaction with the compound of Formula 1. Examples of inorganic acids used in the formation of acid addition salts include hydrochloric acid, bromic acid, sulfuric acid, phosphoric acid, nitric acid, etc. Examples of organic acids include maleic acid, fumaric acid, citric acid, succinic acid, oxalic acid, tartaric acid, methane sulfonic acid, ethane sulfonic acid, benzene sulfonic acid, p-toluene sulfonic acid, naphthalene-2-sulfonic acid, naphthalene-1,5-disulfonic acid, (+)-camphor-10-sulfonic acid, etc.

Hydrochloride, Methanesulfonate, and Ethanesulfonate of compound of Formula 1, and Crystalline Forms Thereof Provided are hydrochloride, methanesulfonate, and ethanesulfonate of the compound of the following Formula 1, i.e., N-(3-(2-(4-(4-methylpiperazin-1-yl)phenylamino)furo[3,2-d]pyrimidin-4-yloxy)phenyl)acrylamide, and crystalline forms thereof:

[Formula 1]

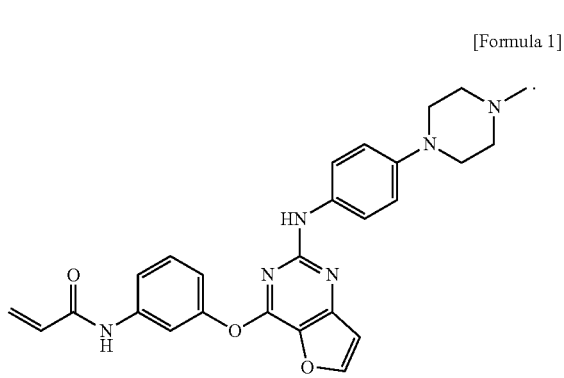 [SMILES: C=CC(=O)Nc1cccc(Oc2nc(Nc3ccc(N4CCN(C)CC4)cc3)nc3ccoc23)c1]

The compound of Formula 1 may be prepared according to general procedures described in Korean Patent No. 1,589,114 and International Patent Publication No. 2011162515, and the contents of these publications disclosed as references herein are incorporated in the present disclosure.

The compound of Formula 1 described in the publication has an amorphous form and is a poorly soluble compound having solubility of less than 0.001 mg/mL for water.

Generally, conversion of a free base to a salt form is known to aid solubilization of a poorly water-soluble drug. However, the salt is required to have overall physicochemical properties pharmaceutically required, such as reproducibility in the preparation of a particular crystalline form, high crystallinity, stability of crystalline forms, chemical stability, non-hygroscopicity, etc.

To select appropriate salt forms of the compound of Formula 1, formation of salts of the compound of Formula 1 by using various acids and solvents according to different conditions and procedures was explored, and physicochemical properties such as solubility, hygroscopicity, stability, etc. of the produced salts were evaluated. Among the prepared salts, crystalline forms of hydrochloride, methanesulfonate, and ethanesulfonate of the compound of Formula 1 are the most excellent in terms of overall physicochemical properties pharmaceutically required, such as reproducibility in the preparation of a particular crystalline form, purity improvement, high crystallinity, stability of crystalline forms, chemical stability, non-hygroscopicity, etc.

Crystalline Forms of Hydrochloride, Methanesulfonate, and Ethanesulfonate of Compound of Formula 1.

The salts of the compound of Formula 1 may be prepared in a crystalline form or in an amorphous form, or in a mixture thereof, and specifically, in a crystalline form. The crystalline forms of hydrochloride, methanesulfonate, and ethanesulfonate of the compound of Formula 1 have excellent stability, and thus have physicochemical properties which are suitable for formulation.

The compound of Formula 1 according to the present disclosure may have various crystalline forms of acid addition salts, for example, a crystalline form of dihydrochloride trihydrate ($2HCl·3H_2O$), a crystalline form of monohydrochloride dihydrate ($1HCl·2H_2O$), a crystalline form of monohydrochloride anhydrous (1 HCl), a crystalline form of methanesulfonic anhydride (1MsOH), a crystalline form of methanesulfonate monohydrate ($1MsOH·1H_2O$), and a crystalline form of ethanesulfonic anhydride (1 EsOH) of the compound of Formula 1.

As examined in Experimental Example 1 below, among the crystalline acid addition salts, the crystalline form of dihydrochloride trihydrate ($2HCl·3H_2O$), the crystalline form of methanesulfonic anhydride (1MsOH), the crystalline form of methanesulfonate monohydrate ($1MsOH·1H_2O$), and the crystalline form of ethanesulfonic anhydride (1EsOH) are the most excellent in terms of solubility in water, and the crystalline form of ethanesulfonic anhydride (1EsOH) is the most excellent in terms of solubility. The acid addition salts may be beneficial in terms of non-water absorption/non-water desorption properties and stability, and thus may be useful materials as an active ingredient of a pharmaceutical composition.

Hereinafter, respective crystalline forms according to the present disclosure will be described in more detail.

According to a specific embodiment, the present disclosure provides a crystalline form of dihydrochloride trihydrate ($2HCl·3H_2O$) of the compound of Formula 1, wherein the crystalline form has an X-ray powder diffraction (XRPD) spectrum including peaks at diffraction angles ($2θ±0.2°$) of 6.4°, 7.1°, 11.1°, 12.8°, and 21.2°, when irradiated with a Cu-Kα light source. More specifically, the crystalline form of dihydrochloride trihydrate ($2HCl·3H_2O$) of the compound of Formula 1 may have an XRPD spectrum including peaks at diffraction angles ($2θ±0.2°$) of 6.4°, 7.1°, 12.8°, 15.6°, 19.6°, 21.2°, 27.9°, and 28.3°, when irradiated with a Cu-Kα light source. These peaks may be peaks having a relative intensity of about 10% or more.

The crystalline form of dihydrochloride trihydrate ($2HCl·3H_2O$) of the compound of Formula 1 may have a water content (a theoretical water content of 9.04%) of about 8.5% to about 9.5% and a melting point of about 210° C. to about 220° C. The crystalline form may have two endothermic peaks at about 75° C. to about 80° C. and about 105° C. to about 110° C. in DSC (10° C./min), indicating a dehydration point of trihydrate. The crystalline form may have an endothermic peak at about 200° C. to about 220° C., indicating a melting point. The crystalline form may have an exothermic peak at about 240° C. to about 250° C., indicating thermal decomposition. In dynamic vapor sorption (DVS) of the crystalline form, water absorption may occur in the region with a relative humidity of 10% to 20%, and very low hygroscopicity may be measured in the region with a relative humidity of 30% to 90%.

According to a specific embodiment, the present disclosure provides a crystalline form of monohydrochloride dihydrate ($1HCl·2H_2O$) of the compound of Formula 1, wherein the crystalline form has an XRPD spectrum including peaks at diffraction angles ($2θ±0.2°$) of 7.0°, 7.9°, 15.8°, 17.2°, 18.6°, 20.6°, 21.3°, and 23.2°, when irradiated with a Cu-Kα light source. More specifically, the crystalline form of monohydrochloride dihydrate ($1HCl·2H_2O$) of the compound of Formula 1 may have an XRPD spectrum including peaks at diffraction angles ($2θ±0.2°$) of 7.0°, 7.9°, 12.6°, 15.8°, 17.2°, 18.6°, 20.2°, 20.6°, 21.0°, 21.3°, 23.2°, 26.9°, and 28.9°, when irradiated with a Cu-Kα light source. These peaks may be peaks having a relative intensity of about 25% or more.

The crystalline form of monohydrochloride dihydrate ($1HCl·2H_2O$) of the compound of Formula 1 may have an endothermic peak at about 110° C. to about 140° C. in DSC (10° C./min), indicating a dehydration point of dihydrate. The crystalline form may have an endothermic peak at about 160° C. to about 170° C., indicating a melting point. The crystalline form may have a water content (a theoretical water content of 6.63%) of about 6.5% to about 7.5% and a melting point of about 150° C. to about 170° C. In DVS of the crystalline form, very low hygroscopicity may be measured in the region with a relative humidity of 10% to 90%.

According to a specific embodiment, the present disclosure provides a crystalline form of monohydrochloride anhydrous (1HCl) of the compound of Formula 1, wherein the crystalline form has an XRPD spectrum including peaks at diffraction angles (2θ±0.2°) of 4.9°, 14.8°, and 21.2°, when irradiated with a Cu-Kα light source. More specifically, the crystalline form of monohydrochloride anhydrous (1HCl) of the compound of Formula 1 may have an XRPD spectrum including peaks at diffraction angles (2θ±0.2°) of 4.9°, 12.2°, 14.8°, 21.2°, 23.1°, and 24.9°, when irradiated with a Cu-Kα light source. These peaks may be peaks having a relative intensity of about 5% or more.

The crystalline form of monohydrochloride anhydrous (1HCl) of the compound of Formula 1 may have an endothermic peak at about 250° C. to about 270° C. in DSC (10° C./min), indicating a melting point. The crystalline form may have a water content (a theoretical water content of 0%) of about 0.1% to about 1.0% and a melting point of about 255° C. to about 270° C. In DVS of the crystalline form, very low hygroscopicity may be measured in the region with a relative humidity of 10% to 90%.

According to a specific embodiment, the present disclosure provides a crystalline form of methanesulfonic anhydride (1MsOH) of the compound of Formula 1, wherein the crystalline form has an XRPD spectrum including peaks at diffraction angles (2θ±0.2°) of 11.8°, 17.2°, 19.0°, 20.0°, 22.8°, and 24.0°, when irradiated with a Cu-Kα light source. More specifically, the crystalline form of methanesulfonic anhydride (1MsOH) of the compound of Formula 1 may have an XRPD spectrum including peaks at diffraction angles (2θ±0.2°) of 10.7°, 11.3°, 11.8°, 12.2°, 15.0°, 17.2°, 17.6°, 18.6°, 19.0°, 20.0°, 22.3°, 22.8°, 23.3°, 23.7°, and 24.0°, when irradiated with a Cu-Kα light source. These peaks may be peaks having a relative intensity of about 15% or more.

The crystalline form of methanesulfonic anhydride (1MsOH) of the compound of Formula 1 may have a water content (a theoretical water content of 0%) of about 0.5% to about 1.5% and a melting point of about 235° C. to about 245° C. The crystalline form may have an endothermic peak at about 235° C. to about 240° C. in DSC (10° C./min), indicating a melting point. In DVS of the crystalline form, hygroscopicity of 2% to 3% may be measured in the region with a relative humidity of 10% to 90%.

According to a specific embodiment, the present disclosure provides a crystalline form of methanesulfonate monohydrate (1MsOH·1H$_2$O) of the compound of Formula 1, wherein the crystalline form has an XRPD spectrum including peaks at diffraction angles (2θ±0.2°) of 7.6°, 15.2°, 17.0°, 18.7°, 20.8°, and 22.8°, when irradiated with a Cu-Kα light source. More specifically, the crystalline form of methanesulfonate monohydrate (1MsOH·1H$_2$O) of the compound of Formula 1 may have an XRPD spectrum including peaks at diffraction angles (2θ±0.2°) of 7.6°, 8.8°, 15.2°, 17.0°, 17.8°, 18.4°, 18.7°, 20.1°, 20.8°, 21.0°, 22.1°, 22.8°, 24.6°, 24.9°, 25.4°, 26.1°, 26.5°, 27.0°, and 28.4°, when irradiated with a Cu-Kα light source. These peaks may be peaks having a relative intensity of about 15% or more.

The crystalline form of methanesulfonate monohydrate (1MsOH·1H$_2$O) of the compound of Formula 1 may have an endothermic peak at about 90° C. to about 95° C. in DSC (10° C./min), indicating a dehydration point of monohydrate. The crystalline form may have an endothermic peak at about 205° C. to about 210° C., indicating a melting point. The crystalline form may have a water content (a theoretical water content of 3.08%) of about 2.5% to about 3.5% and a melting point of about 200° C. to about 210° C. In DVS of the crystalline form, very low hygroscopicity may be measured in the region with a relative humidity of 10% to 90%.

According to a specific embodiment, the present disclosure provides a crystalline form of ethanesulfonic anhydride (1 EsOH) of the compound of Formula 1, wherein the crystalline form has an XRPD spectrum including peaks at diffraction angles (2θ±0.2°) of 17.1°, 18.6°, 21.3°, 22.3°, 23.0°, and 23.6°, when irradiated with a Cu-Kα light source. More specifically, the crystalline form of ethanesulfonic anhydride (1EsOH) of the compound of Formula 1 may have an XRPD spectrum including peaks at diffraction angles (2θ±0.2°) of 7.1°, 11.1°, 11.7°, 14.2°, 17.1°, 18.1°, 18.6°, 19.8°, 20.0°, 21.3°, 22.3°, 23.0°, and 23.6°, when irradiated with a Cu-Kα light source. These peaks may be peaks having a relative intensity of about 15% or more.

The crystalline form of ethanesulfonic anhydride (1 EsOH) of the compound of Formula 1 may have an endothermic peak at about 230° C. to about 240° C. in DSC (10° C./min), indicating a melting point. The crystalline form may have a water content (a theoretical water content of 0%) of about 0.1% to about 1.0% and a melting point of about 230° C. to about 240° C. In DVS of the crystalline form, very low hygroscopicity of less than 1% may be measured in the region with a relative humidity of 10% to 90%.

Pharmaceutical Composition

As described in Korean Patent No. 1,589,114 and International Patent Publication No. 2011162515, the compound of Formula 1 was demonstrated to have a selective and effective inhibitory activity against cancer cell growth and drug resistance caused by epithelial cell growth factor receptor (EGFR) tyrosine kinase or a variant thereof.

In this point of view, crystal forms of hydrochloride, methanesulfonate, and ethanesulfonate of the compound of Formula 1 may be used in preparing a pharmaceutical composition for treating or preventing benign or malignant tumors, inflammatory diseases, or autoimmune diseases such as rheumatoid arthritis, which are caused by EGFR tyrosine kinase or a variant thereof.

Therefore, the present disclosure provides a pharmaceutical composition including the crystal form of hydrochloride, methanesulfonate, or ethanesulfonate of the compound of Formula 1 and one or more pharmaceutically acceptable carriers or diluents. The pharmaceutical composition may be used for the treatment of cancers, tumors, inflammatory diseases, or autoimmune diseases such as rheumatoid arthritis, which are caused by EGFR tyrosine kinase or a variant thereof.

An administration dose of the crystalline form of hydrochloride, methanesulfonate, or ethanesulfonate of the compound of Formula 1 or a pharmaceutical composition including the same may vary depending on a subject to be treated, severity of illness or state, administration rate, physician's decision, etc., but the free base of the compound of Formula 1 may be generally administered to a human subject having a body weight of 70 kg via an oral or parenteral administration route in an amount of 10 mg to 2,000 mg, specifically, in an amount of 50 mg to 1,000 mg, as an active ingredients based on the compound of Formula 1, once to four times daily or on an on/off schedule. In some cases, it may be more appropriate to administer a lower dosage than that mentioned above, a higher dosage than the above may be administered if it does not cause harmful side effects, and in the case when a significantly larger dosage is to be administered, the administration may be performed daily by several divided doses with a lesser dosage per administration.

The pharmaceutical composition according to the present disclosure may be formulated according to common methods in various formulations for oral administration, e.g., tablets, pills, powders, capsules, syrups, emulsions, microemulsions, etc., or for parenteral administration, e.g., intramuscular, intravenous, or subcutaneous administrations.

The pharmaceutical composition may include any common non-toxic, pharmaceutically acceptable carrier, diluent, auxiliary agent, excipient, etc. When the pharmaceutical composition according to the present disclosure is prepared as a formulation for oral administration, examples of the carrier to be used may include cellulose, calcium silicate, corn starch, lactose, sucrose, dextrose, calcium phosphate, stearic acid, magnesium stearate, calcium stearate, gelatin, talc, surfactants, suspending agents, emulsifying agents, diluents, etc. Additionally, when the pharmaceutical composition is prepared as a formulation for oral administration, examples of the diluents to be used may include lactose, mannitol, saccharide, microcrystalline cellulose, cellulose derivative, dry corn starch, etc. When the pharmaceutical composition according to the present disclosure is prepared as a formulation for injections, the carrier may include water, saline, an aqueous glucose solution, an aqueous sugar-like solution, alcohols, glycols, ethers (e.g., polyethyleneglycol 400), oils, fatty acids, fatty acid esters, glycerides, surfactants, suspending agents, emulsifying agents, etc.

Further, provided is a method of treating a disease, the method including administering to a subject a therapeutically effective amount of the crystalline form of the compound of Formula 1 or the pharmaceutical composition. The disease may be benign or malignant tumors, inflammatory diseases, or autoimmune diseases such as rheumatoid arthritis.

Hereinafter, the present disclosure will be described with reference to specific exemplary embodiments. However, these exemplary embodiments are for illustrative purposes only, and the scope of the present disclosure is not intended to be limited thereby.

Analysis Apparatus and Method of Measurement

1. X-Ray Powder Diffraction (XRPD)

XRPD analyses of samples were performed in the range from 3° 2θ to 40° 2θ using a D8 Advance (Bruker ASX, Germany) analyzer. When the amount of a sample was less than 100 mg, about 5 mg to 10 mg of the sample was gently compressed on a glass slide which was fit into a sample holder. When the amount of a sample was more than 100 mg, about 100 mg of the sample was gently compressed in a plastic sample holder so that the sample surface became flat and positioned immediately on top of the sample holder level.

The measurement was performed as follows:
Anode material (Kα): Cu Ka (1.54056 Å)
Scan range: 3° to 40°
Generator settings: 100 mA, 40.0 kV
Scan speed: 1 sec/step
Diver slit: 0.3°
Anti-scatter slit: 0.3°
Temperature: 20° C.
Step size: 0.02° 2θ
Rotating: use
Goniometer radius: 435 mm 2. Differential Scanning Calorimeter (DSC)

DSC analysis was performed in an STA-1000 (Scinco, Korea) analyzer at 30° C. to 350° C. 5 mg to 10 mg of a sample was weighed and added into an aluminum DSC pan, and the pan was sealed with a perforated aluminum lid in a non-sealing manner. Then, the sample was heated at a scan speed of 10° C./min from 30° C. to 350° C., and the heat flow reaction (DSC) generated was monitored.

3. Dynamic Vapor Sorption (DVS)

DVS analysis was performed in a DVS advantage (Surface measurement system, United Kingdom) analyzer at 25° C. with a relative humidity of 0% to 90%. 10 mg of a sample was placed into a wire-mesh vapor sorption balance pan, and then attached to a DVS-advantage dynamic vapor sorption balance via surface measurement systems. Until a stable weight was achieved (99.5% completion of steps), the sample was applied to a ramping profile with a relative humidity (RH) of 10% to 90% with a 10% increase of the sample while maintaining the sample in each step. Upon completion of the sorption cycle, the sample was dried using the same process while maintaining a relative humidity of below 0%. The changes in the sample weight during the adsorption/desorption cycle (repeated 3 times) were recorded, and the hygroscopicity of the sample was measured.

4. High Performance Liquid Chromatography (HPLC)

HPLC analysis was performed for analyzing purity and contents such as a stability test, etc., using an Agilent 1100/1200 series HPLC Systems (Agilent, USA) analyzer, and the conditions used for HPLC were as follows.

Purity and Content Analysis Conditions: Furopyrimidine Compound of Formula 1
Column: Hydrosphere C18 (YMC), 5 μm (150 mm×4.6 mm)
Column temperature: 30° C.
Detector: UV spectrophotometer
Detection wavelength: 254 nm
Flow rate: 1.0 mL/min
Time of analysis: 35 min
Eluent: $NaClO_4$—$NaH_2PO_4$— phosphate buffer solution (pH 2.5±0.1)/$CH_3CN$=65/35(v/v %)

5. Ion Chromatography (IC)

IC analysis was performed for analyzing the hydrochloric acid content of hydrochloride using a Thermo Fisher Scientific ICS-2500 series IC System (Thermo Fisher Scientific, USA) analyzer, and the conditions for IC analysis were as follows.

Content analysis conditions: Furopyrimidine Compound of Formula 1
Column: IonPac AS19 (Dionex), (250 mm×4 mm), guard (50 mm×4 mm)
Column temperature: 30° C.
Detector: conductivity detector (CD)
Suppressor: ASRS 4 mm, current 40 mA
Flow rate: 1.0 mL/min
Analysis time: 30 min
Eluent: 10 mM potassium hydroxide solution 6. Measurement of Water Content Measurement of water content was performed using a Karl-Fischer Titrator 795KFT Titrino (Metrohm, Switzerland).

7. Measurement of Melting Point

A melting point was measured using a melting point analyzer IA9200 (Electrothermal, UK).

EXAMPLES: PREPARATION AND ANALYSIS OF CRYSTALLINE FORMS OF ACID ADDITION SALTS OF COMPOUND OF FORMULA 1

Example 1. Preparation of Crystalline Form of Dihydrochloride Trihydrate ($2HCl \cdot 3H_2O$) of Compound of Formula 1

690 g (1.47 mol) of a compound of Formula 1 prepared according to methods of Korean Patent No. 1,589,114 and International Patent Publication No. 2011162515 cited herein or a method similar thereto was added to 6,900 mL of a 80% aqueous isopropanol solution (isopropane/water=8/2). After adding 240 mL (2.93 mol) of concentrated hydrochloric acid to the reaction solution, the mixture was stirred at room temperature for 12 hr. The reaction solution was cooled to 10° C., and the precipitated solid was filtered. After washing with 690 mL of 80% aqueous isopropanol solution (isopropanol/water=8/2) and drying, 650 g of the title compound (yield: 82.0%) was obtained.

Water content: 8.8% (a theoretical value of trihydrate: 9.04%)

Ion chromatography: 13.6% (a theoretical value of dihydrochloride: 13.4%)

Analysis of Characteristics

Figure 2A:
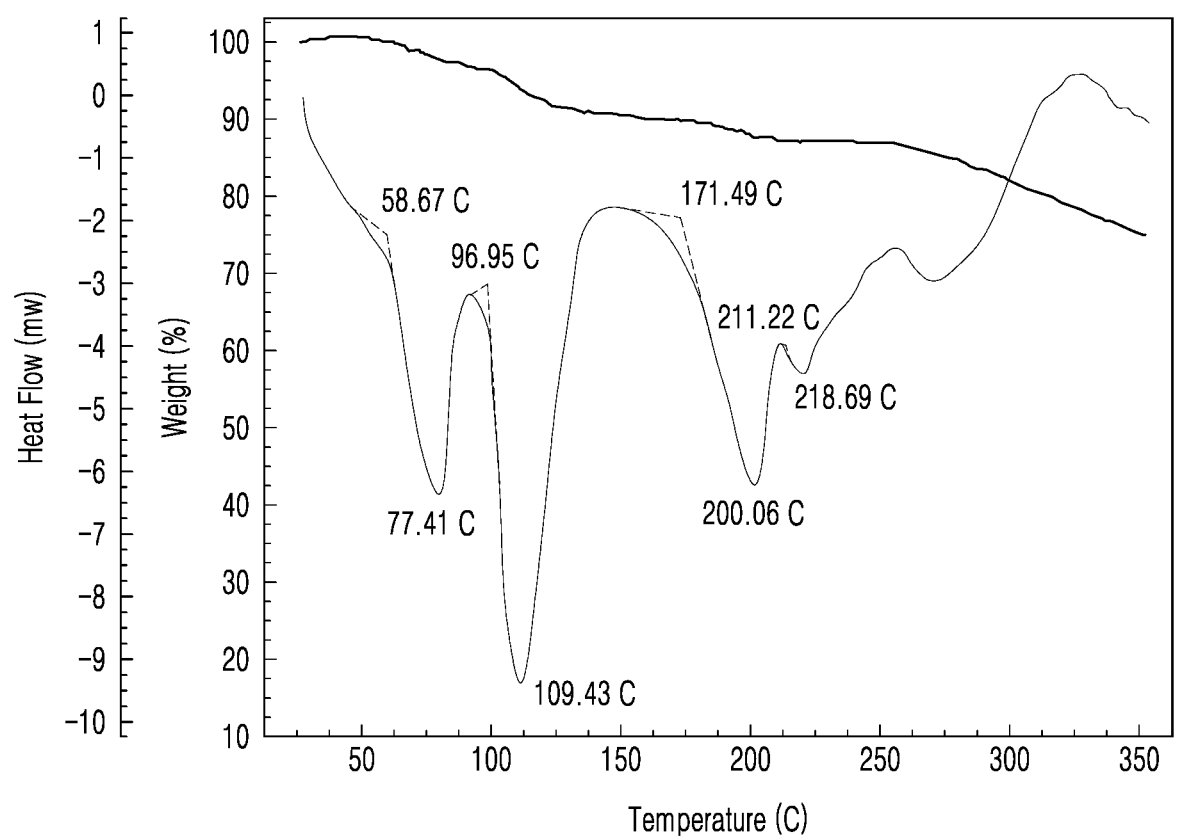
FIGS. 2A to 2F show differential scanning calorimetry (DSC) curves of crystalline forms of acid addition salts of the compound of Formula 1 according to exemplary embodiments.
Figure 3A:
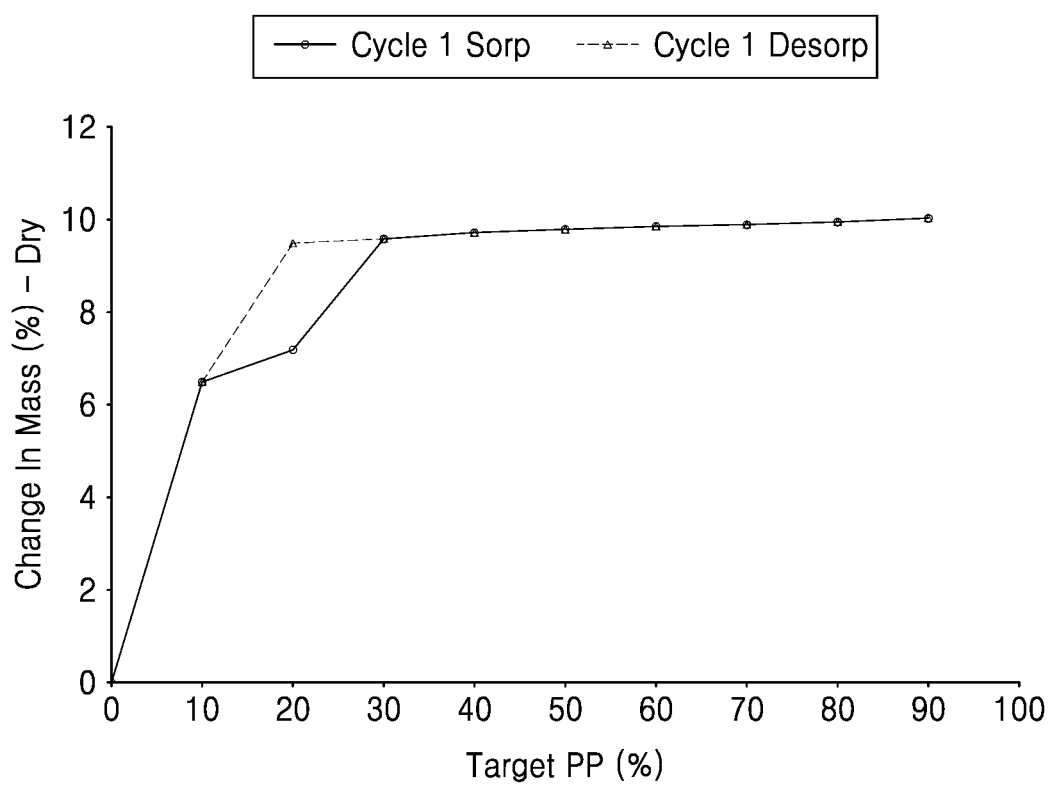
FIGS. 3A to 3F show dynamic vapor sorption (DVS) curves of crystalline forms of acid addition salts of the compound of Formula 1 according to exemplary embodiments.

Results of XRPD, DSC, and DVS analyses of the crystalline form prepared in Example 1 are shown in FIGS. 1A, 2A, and 3A, respectively.

The peaks having a relative intensity (I/Io) of 3% or higher in the XRPD spectrum of the above crystalline form are shown in Table 1 below. When the peaks had I/Io ratios equal to or higher than 10%, they appeared at diffraction angles (2θ±0.2°) of 6.4°, 7.1°, 12.8°, 15.6°, 19.6°, 21.2°, 27.9°, and 28.3°.

TABLE 1

| 2θ (±0.2) | d | I/I$_o$ (%) |
|---|---|---|
| 6.4 | 13.8 | 100.0 |
| 7.1 | 12.4 | 15.4 |
| 8.8 | 10.0 | 8.1 |
| 12.8 | 6.9 | 44.5 |
| 13.4 | 6.6 | 5 |
| 13.8 | 6.4 | 3.8 |
| 14.2 | 6.2 | 6.2 |
| 15.6 | 8.1 | 14 |
| 16.6 | 5.3 | 8.3 |
| 17.4 | 5.1 | 6.7 |
| 17.7 | 5.0 | 5.4 |
| 18.2 | 4.9 | 4 |
| 18.4 | 4.8 | 6.9 |
| 19.3 | 4.6 | 7.4 |
| 19.6 | 4.5 | 10.7 |
| 20.6 | 4.3 | 6.6 |
| 21.2 | 4.2 | 19 |
| 21.5 | 4.1 | 5 |
| 22.3 | 4.0 | 5 |
| 22.5 | 3.9 | 3.6 |
| 23.2 | 3.8 | 6.9 |
| 24.9 | 3.6 | 8.8 |
| 25.7 | 3.5 | 7.3 |
| 26.5 | 3.4 | 5 |
| 26.9 | 3.3 | 7.3 |
| 27.9 | 3.2 | 11.9 |
| 28.3 | 3.2 | 10.2 |
| 28.6 | 3.1 | 4.3 |
| 29.7 | 3.0 | 3.5 |
| 30.3 | 3.0 | 5.5 |
| 31.0 | 2.9 | 5.7 |
| 33.5 | 2.7 | 4.5 |
| 36.1 | 2.5 | 3.8 |
| 37.5 | 2.4 | 3.8 |
| 37.9 | 2.4 | 3.6 |
| 39.7 | 2.3 | 5.2 |

2θ: diffraction angle, d: distance between crystal faces,
I/I$_o$ (%): relative intensity (I indicates the intensity of each peak; I$_o$ indicates the intensity of the highest peak)

The above crystalline form showed an endothermic peak which has a starting point at about 58.7° C. and its lowest point at about 77.4° C. and about 109.4°, and endothermic peaks at about 200.1° C. and about 218.7° C. and an exothermic peak at about 250° C. in a DSC (10° C./min). In the DSC, the endothermic peaks at about 77.4° C. and about 109.4° C. indicate a dehydration point of the crystalline form of dihydrochloride trihydrate, the endothermic peaks at about 200.08° C. and about 218.69° C. indicate a melting point, and the exothermic peak at about 250° C. indicates thermal decomposition.

The crystalline form showed a water content of about 8.8% (a theoretical water content of 9.04%) in a Karl-Fischer titrator and a melting point of about 210° C. to about 218° C.

In the DVS, the above crystalline form showed water absorption in the region with a relative humidity of 0% to 20%, but very low water absorption in the region with a relative humidity of 30% or more. The crystalline form was sufficiently stable under long-term storage conditions (e.g., a temperature of 25° C. and a relative humidity of 60%), accelerated conditions (e.g., a temperature of 40° C. and a relative humidity of 75%), and harsh conditions (e.g., a temperature of 40° C. and a relative humidity of 75%).

Example 2. Preparation of Crystalline Form of Monohydrochloride Dihydrate (1HCl·2H$_2$O) of Compound of Formula 1

Example 2.1. Preparation from Dihydrochloride Trihydrate (2HCl·3H$_2$O) of Compound of Formula 1

460 g (0.85 mol) of the dihydrochloride trihydrate (2HCl·3H$_2$O) of the compound of Formula 1 was added to 4,600 mL of a 50% aqueous ethanol solution (ethanol/water=5/5). The reaction solution was raised to a temperature of 40° C. to 45° C., and an aqueous solution of 67.7 g (1.69 mol) of sodium hydroxide in 460 mL of water was added thereto, followed by stirring at 40° C. to 45° C. for 30 min. After adding 89.7 mL (1.02 mol) of concentrated hydrochloric acid to the reaction solution, the mixture was stirred at 40° C. to 45° C. for 1 hr. The reaction solution was slowly cooled to 20° C. to 25° C., and stirred at 20° C. to 25° C. for 12 hr. The precipitated solid was filtered, and washed with 460 mL of a 50% cold aqueous ethanol solution (ethanol/water=5/5), and dried to obtain 398 g of the title compound (yield: 87.0%).

Water content: 7.5% (a theoretical value of dihydrate: 6.63%)

Ion chromatography: 7.4% (a theoretical value of monohydrochloride: 7.2%)

Example 2.2. Preparation from Compound of Formula 1

53 g (0.11 mol) of the compound of Formula 1 was added to 530 mL of an 80% aqueous methanol solution (methanol/water=8/2). After adding 10.9 mL (0.12 mol) of concentrated hydrochloric acid to the reaction solution, the mixture was stirred at 20° C. to 25° C. for 12 hr. The precipitated solid was filtered. After washing with 53 mL of an 80% aqueous methanol solution (methanol/water=8/2) and drying at 50° C., 49 g of the title compound (yield: 80.0%) was obtained.

Water content: 6.2% (a theoretical value of dihydrate: 6.63%)

Ion chromatography: 7.0% (a theoretical value of monohydrochloride: 7.2%)

Analysis of Characteristics

Figure 1B:
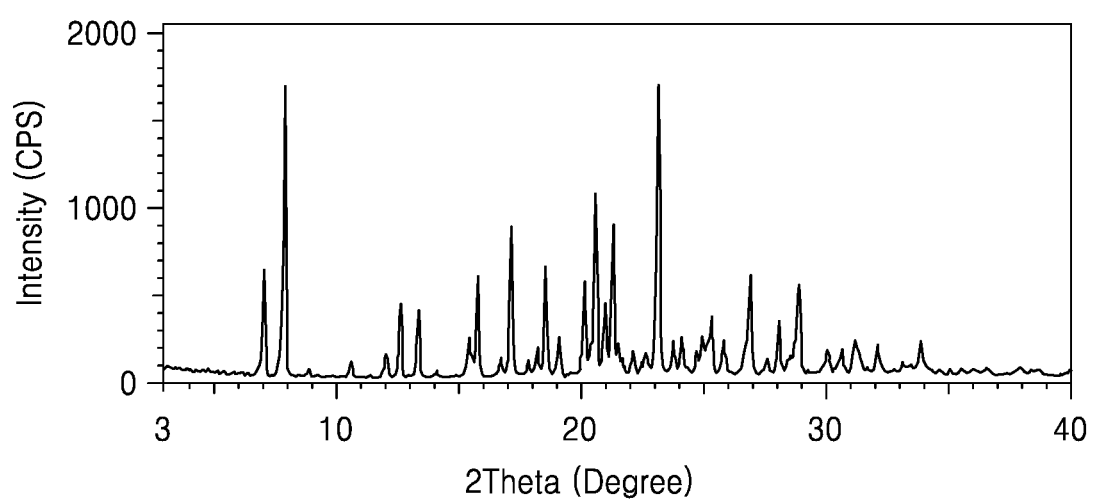
Figure 2B:
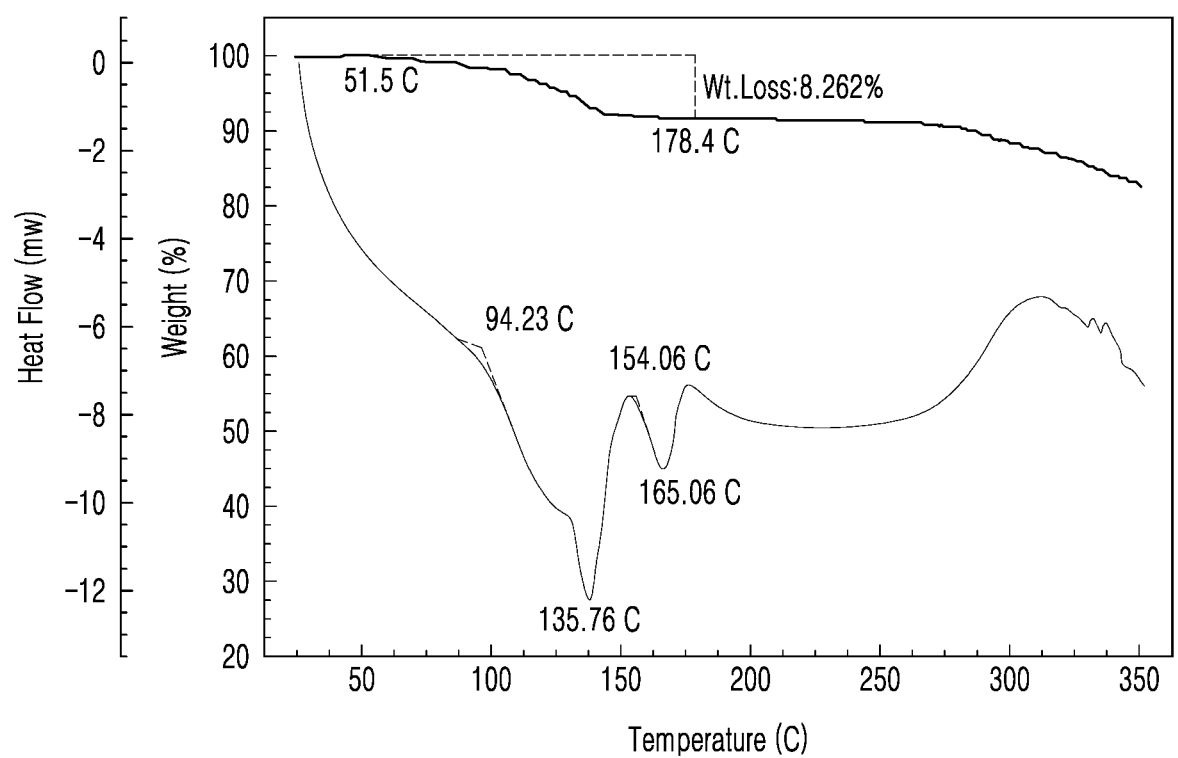
Figure 3B:
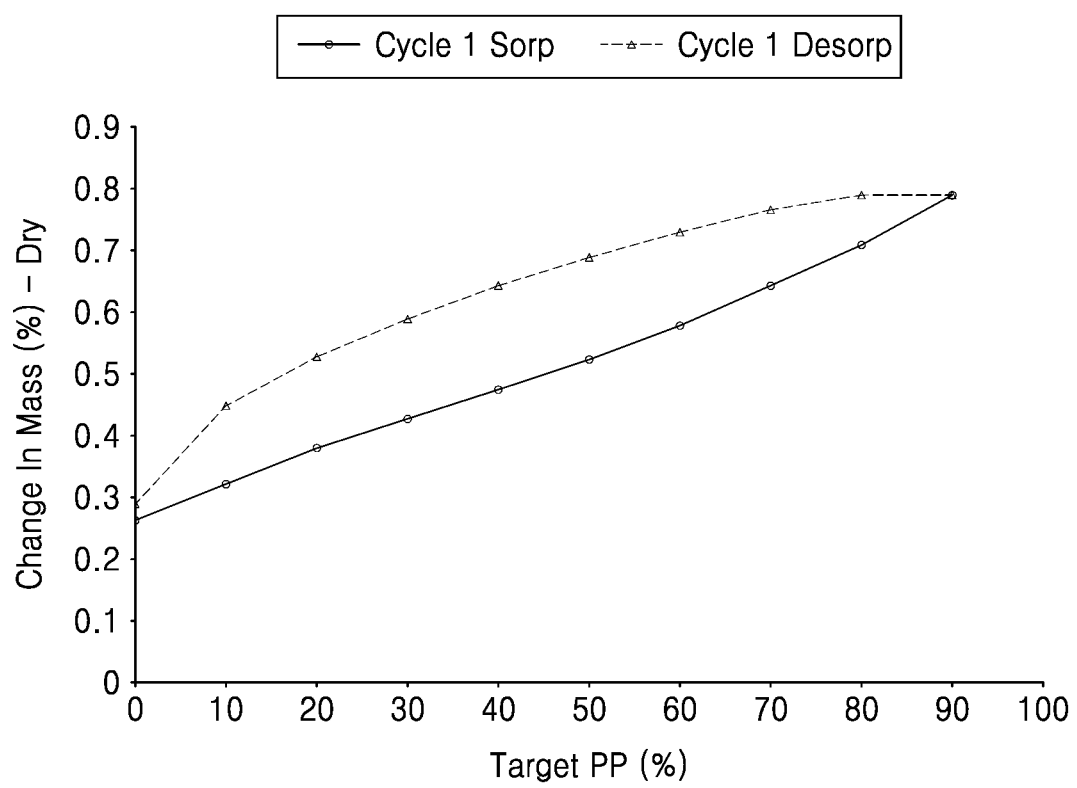

Results of XRPD, DSC, and DVS analyses of the crystalline form prepared in Example 2 are shown in FIGS. 1B, 2B, and 3B, respectively.

The peaks having a relative intensity (I/Io) of 5% or higher in the XRPD spectrum of the above crystalline form are shown in Table 2 below. When the peaks had I/Io ratios equal to or higher than 10%, they appeared at diffraction angles (2θ±0.2°) of 7.0°, 7.9°, 12.6°, 13.4°, 15.5°, 15.8°, 17.2°, 18.2°, 18.6°, 19.1°, 20.2°, 20.6°, 21.0°, 21.3°, 22.1°, 23.2°, 23.8°, 24.1°, 24.8°, 25.0°, 25.3°, 25.9°, 26.9°, 28.1°, 28.9°, 30.1°, 30.7°, 31.2°, 32.2°, and 33.9°.

TABLE 2

| 2θ (±0.2) | d | I/I$_o$ (%) |
|---|---|---|
| 7.0 | 12.6 | 37.4 |
| 7.9 | 11.2 | 99.8 |
| 10.6 | 8.3 | 6.1 |
| 12.0 | 7.3 | 9.1 |
| 12.6 | 7.0 | 26.1 |
| 13.4 | 6.6 | 24.1 |
| 15.5 | 5.7 | 15 |
| 15.8 | 5.6 | 35.6 |
| 16.7 | 5.3 | 7.8 |
| 17.2 | 5.2 | 52 |
| 17.9 | 5.0 | 7 |
| 18.2 | 4.9 | 11.4 |
| 18.6 | 4.8 | 38.4 |
| 19.1 | 4.6 | 15.1 |
| 20.2 | 4.4 | 33.9 |
| 20.6 | 4.3 | 26.1 |
| 21.0 | 4.2 | 26.1 |
| 21.3 | 4.2 | 53.2 |
| 22.1 | 4.0 | 99 |
| 22.7 | 3.9 | 9.5 |
| 23.2 | 3.8 | 100 |
| 23.8 | 3.7 | 14.1 |
| 24.1 | 3.7 | 15 |
| 24.8 | 3.6 | 10.1 |
| 25.0 | 3.6 | 15.3 |
| 25.3 | 3.5 | 21.4 |
| 25.9 | 3.4 | 14 |
| 26.9 | 3.3 | 35.9 |
| 27.6 | 3.2 | 7.8 |
| 28.1 | 3.2 | 20.6 |
| 28.5 | 3.1 | 9.3 |
| 28.9 | 3.1 | 32.8 |
| 30.1 | 3.0 | 10.7 |
| 30.7 | 2.9 | 10.6 |
| 31.2 | 2.9 | 14.1 |
| 32.2 | 2.8 | 12.3 |
| 33.2 | 2.7 | 6.9 |
| 33.9 | 2.6 | 13.8 |
| 38.0 | 2.4 | 5.1 |

2θ: diffraction angle, d: distance between crystal faces,
I/I$_o$ (%): relative intensity (I indicates the intensity of each peak; I$_o$ indicates the intensity of the highest peak)

The above crystalline form showed endothermic peaks at about 115.0° C. and about 135.8° C. and an endothermic peak at about 165.1° C. in a DSC (10° C./min). In the DSC, the endothermic peaks at about 115.0° C. and about 135.8° C. indicate a dehydration point of the crystalline form of monohydrochloride dihydrate, and the endothermic peak at about 165.1° C. indicates a melting point.

The crystalline form showed a water content of about 7.5% (a theoretical water content of 6.63%) in a Karl-Fischer titrator and a melting point of about 154° C. to about 165° C.

In the DVS, the above crystalline form showed very water absorption of about 0.8% in the region with a relative humidity of 10% to 90%. The crystalline form was sufficiently stable under long-term storage conditions (e.g., a temperature of 25° C. and a relative humidity of 60%) and accelerated conditions (e.g., a temperature of 40° C. and a relative humidity of 75%).

Example 3. Preparation of Crystalline Form of Monohydrochloride Anhydrous (1HCl·Anhydrate) of Compound of Formula 1

Example 3.1. Preparation from Dihydrochloride Trihydrate (2HCl·3H$_2$O) of Compound of Formula 1

70 g of dihydrochloride trihydrate (2HCl·3H$_2$O) of the compound of Formula 1 was added to 2,100 mL of water. The reaction solution was stirred at room temperature for 2 hr, and then precipitated solid was filtered. After washing with 70 mL of water and drying, 25 g of the title compound (yield: 35.7%) was obtained.
Water content: 0.3%
Ion chromatography: 7.1% (a theoretical value of monohydrochloride: 7.2%)

Example 3.2. Preparation from Compound of Formula 1

Figure 1C:
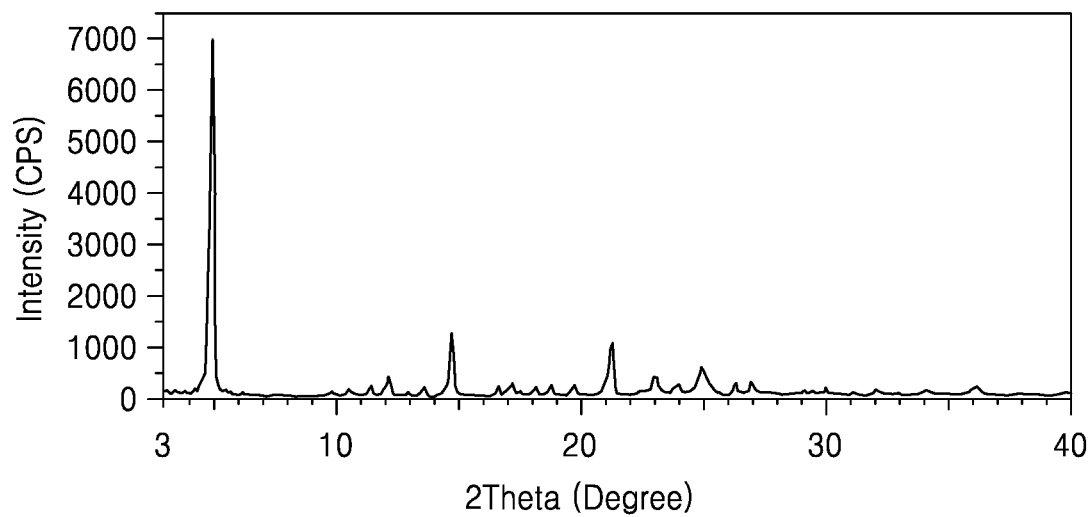
Figure 2C:
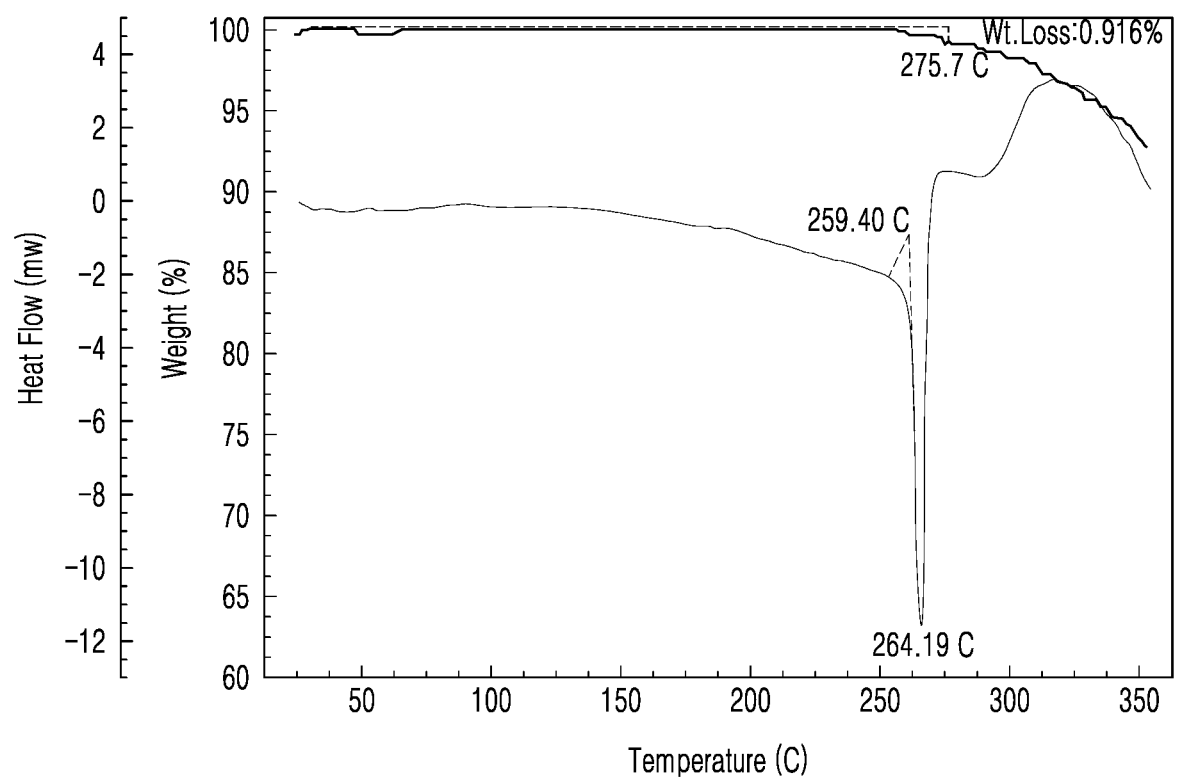
Figure 3C:
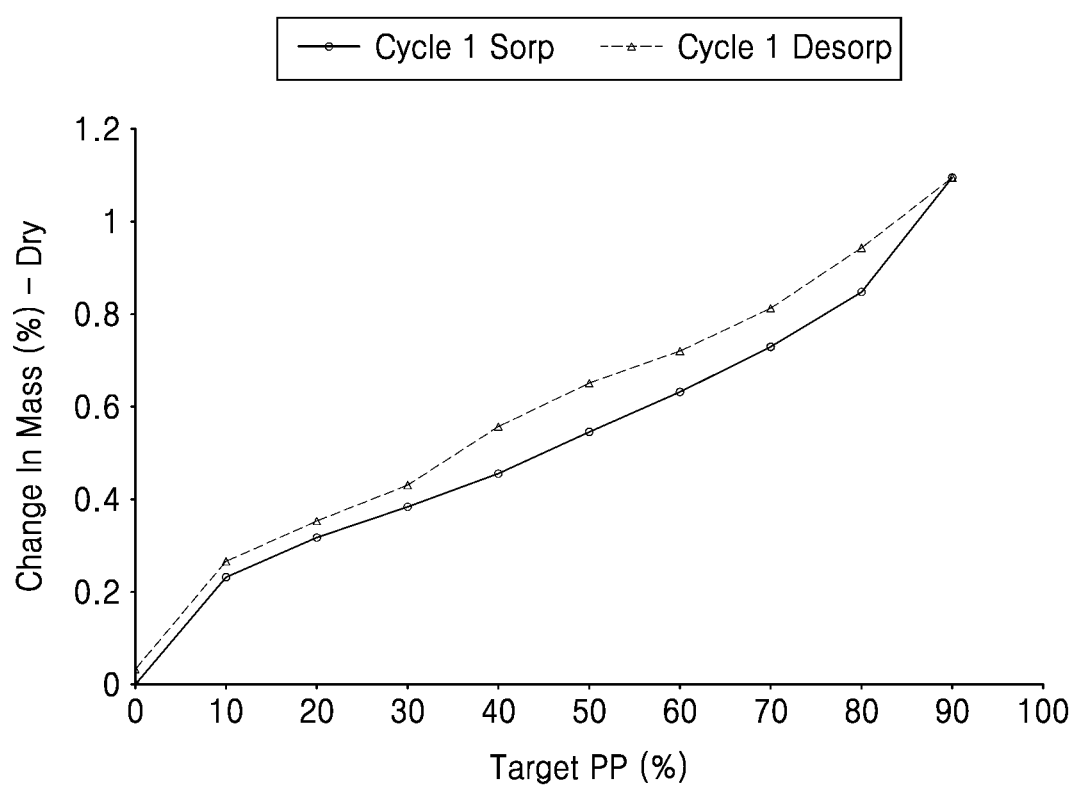

53 g (0.11 mol) of the compound of Formula 1 was added to 530 mL of methanol. After adding 10.9 mL (0.12 mol) of concentrated hydrochloric acid to the reaction solution, the mixture was stirred at 20° C. to 25° C. for 12 hr. The precipitated solid was filtered. After washing with 53 mL of methanol and drying at 50° C., 46 g of the title compound (yield: 81.0%) was obtained.
Water content: 0.4%
Ion chromatography: 7.2% (a theoretical value of monohydrochloride: 7.2%)
Analysis of Characteristics
Results of XRPD, DSC, and DVS analyses of the crystalline form prepared in Example 3 are shown in FIGS. 1C, 2C, and 3C, respectively.

The peaks having a relative intensity (I/I$_0$) of 2% or higher in the XRPD spectrum of the above crystalline form are shown in Table 3 below. When the peaks had I/I$_0$ ratios equal to or higher than 5%, they appeared at diffraction angles (2θ±0.2°) of 4.9°, 12.2°, 14.8°, 21.2°, 23.1°, and 24.9°.

TABLE 3

| 2θ (±0.2) | d | I/I$_o$ (%) |
|---|---|---|
| 4.9 | 17.8 | 100 |
| 10.6 | 8.4 | 2.4 |
| 11.4 | 7.8 | 3.6 |
| 12.2 | 7.3 | 5.6 |
| 13.6 | 6.5 | 2.9 |
| 14.8 | 6.0 | 18.2 |
| 16.6 | 5.3 | 3.1 |
| 17.2 | 5.2 | 3.8 |
| 18.8 | 4.7 | 3.5 |
| 19.8 | 4.5 | 3.4 |
| 21.2 | 4.2 | 14.6 |
| 22.5 | 4.0 | 2.1 |
| 23.1 | 3.9 | 5.3 |
| 24.0 | 3.7 | 3.8 |
| 24.9 | 3.6 | 8.4 |
| 25.2 | 3.5 | 4.6 |
| 26.3 | 3.4 | 3.8 |
| 27.0 | 3.3 | 3.9 |
| 29.1 | 3.1 | 2.6 |
| 30.0 | 3.0 | 2.9 |
| 34.2 | 2.6 | 2.4 |
| 36.1 | 2.5 | 2.7 |

2θ: diffraction angle, d: distance between crystal faces,
I/I$_o$ (%): relative intensity (I indicates the intensity of each peak; I$_o$ indicates the intensity of the highest peak)

The above crystalline form showed an endothermic peak at about 264.2° C. in a DSC (10° C./min). In the DSC, the endothermic peak at about 264.2° C. indicates a melting point.

The crystalline form showed a water content of about 0.3% in a Karl-Fischer titrator and a melting point of about 259° C. to about 264° C.

In the DVS, the above crystalline form showed low water absorption of about 1% in the region with a relative humidity of 10% to 90%. The crystalline form was sufficiently stable under long-term storage conditions (e.g., a temperature of 25° C. and a relative humidity of 60%) and accelerated conditions (e.g., a temperature of 40° C. and a relative humidity of 75%).

Example 4. Preparation of Methanesulfonic Anhydride (Mesylate·Anhydrate) of Compound of Formula 1

10 g (21.26 mmol) of the compound of Formula 1 was added to 100 mL of ethanol. 1.52 mL (23.38 mmol) of methane sulfonic acid was added dropwise to the reaction solution, followed by stirring at 20° C. to 25° C. for 12 hr, and the precipitated solid was filtered. The filtered product was washed with 10 mL of ethanol, and dried at 50° C. to obtain 10 g of the title compound (yield: 83.0%).

Water content: 1.0%
Analysis of Characteristics

Figure 1D:
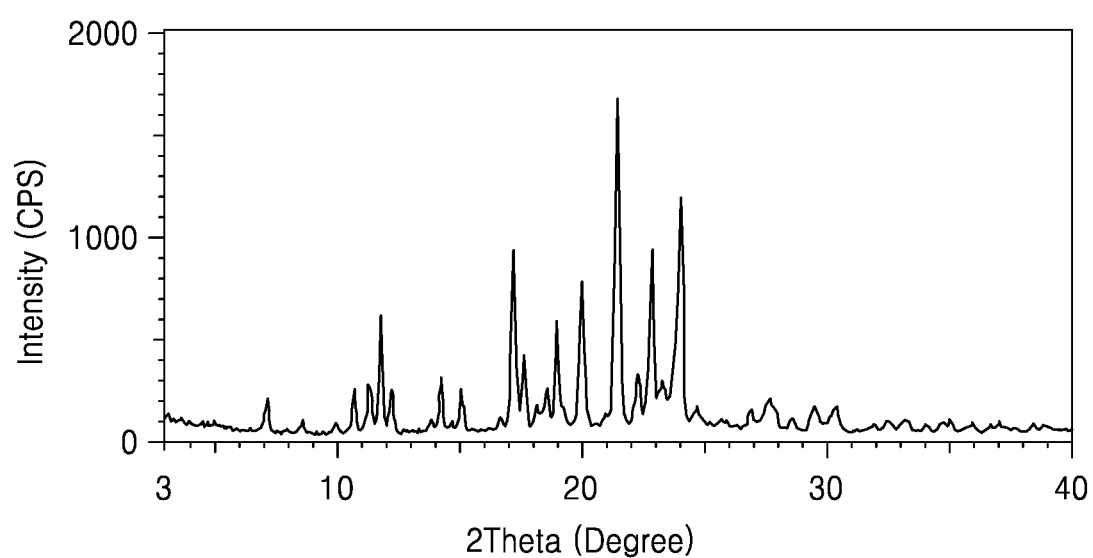
Figure 2D:
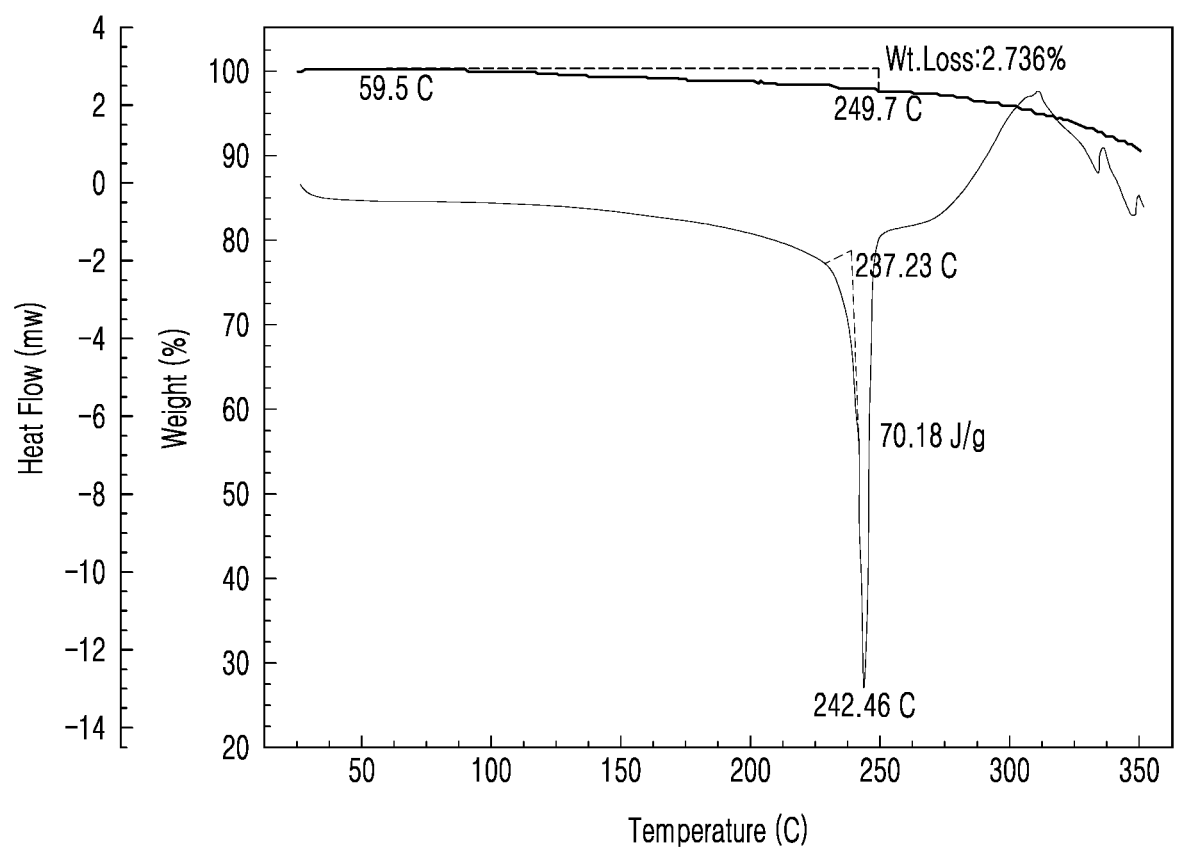
Figure 3D:
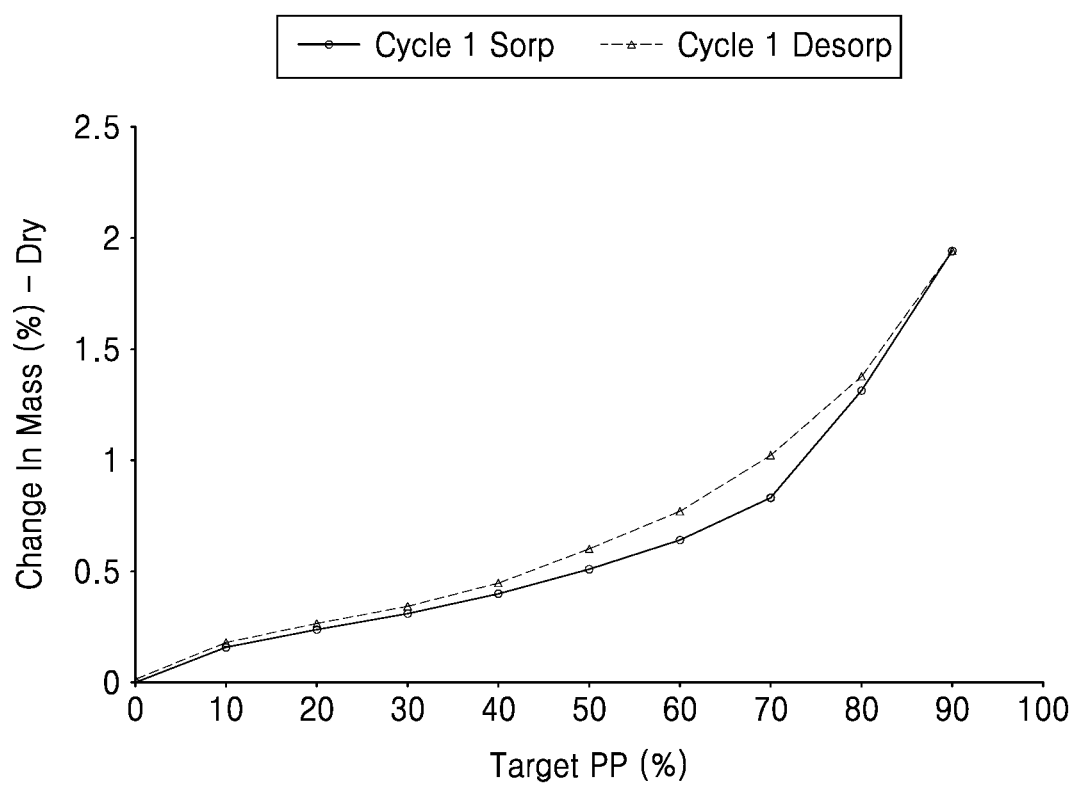

Results of XRPD, DSC, and DVS analyses of the crystalline form of methanesulfonic anhydride (MsOH·anhydrate) of the compound of Formula 1 prepared in Example 4 are shown in FIGS. 1D, 2D, and 3D, respectively.

The peaks having a relative intensity ($I/I_o$) of 5% or higher in the XRPD spectrum of the above crystalline form are shown in Table 4 below. When the peaks had $I/I_0$ ratios equal to or higher than 10%, they appeared at diffraction angles (2θ±0.2°) of 7.1°, 10.7°, 11.3°, 11.8°, 12.2°, 14.2°, 15.0°, 17.2°, 17.6°, 18.1°, 18.6°, 19.0°, 20.0°, 21.4°, 22.3°, 22.8°, 23.3°, 23.7°, 24.0°, 24.7°, 27.5°, 27.7°, and 30.3°.

TABLE 4

| 2θ (±0.2) | d | $I/I_o$ (%) |
|---|---|---|
| 7.1 | 12.4 | 12.1 |
| 8.6 | 10.3 | 6 |
| 9.9 | 8.9 | 5.1 |
| 10.7 | 8.3 | 15.3 |
| 11.3 | 7.8 | 16.1 |
| 11.8 | 7.5 | 36.8 |
| 12.2 | 7.2 | 15 |
| 13.8 | 6.4 | 6.1 |
| 14.2 | 6.2 | 18.1 |
| 15.0 | 5.9 | 15.3 |
| 16.7 | 5.3 | 6.6 |
| 17.2 | 5.1 | 56.6 |
| 17.6 | 5.0 | 25.2 |
| 18.1 | 4.9 | 10.4 |
| 18.6 | 4.8 | 16.4 |
| 19.0 | 4.7 | 35.4 |
| 19.3 | 4.6 | 9.6 |
| 20.0 | 4.4 | 47.1 |
| 21.4 | 4.1 | 100 |
| 22.3 | 4.0 | 20 |
| 22.8 | 3.9 | 56.9 |
| 23.3 | 3.8 | 17.5 |
| 23.7 | 3.7 | 27.3 |
| 24.0 | 3.7 | 72.8 |
| 24.7 | 3.6 | 10.3 |
| 25.2 | 3.5 | 5.6 |
| 25.6 | 3.5 | 5.9 |
| 26.9 | 3.3 | 8.1 |
| 27.5 | 3.2 | 10.2 |
| 27.7 | 3.2 | 13 |
| 28.6 | 3.1 | 6.1 |
| 29.5 | 3.0 | 9.9 |
| 30.3 | 2.9 | 10.2 |
| 32.5 | 2.8 | 6.2 |
| 32.6 | 2.7 | 6 |
| 33.3 | 2.7 | 6.6 |
| 34.7 | 2.6 | 5.6 |
| 35.9 | 2.5 | 5.3 |

2θ: diffraction angle, d: distance between crystal faces,
$I/I_o$ (%): relative intensity (I indicates the intensity of each peak; $I_o$ indicates the intensity of the highest peak)

The above crystalline form showed an endothermic peak at about 242.5° C. in a DSC (10° C./min). In the DSC, the endothermic peak at about 242.5° C. indicates a melting point.

The crystalline form showed a water content of about 1.0% in a Karl-Fischer titrator and a melting point of about 237° C. to about 242° C.

In the DVS, the above crystalline form showed low water absorption of about 2% in the region with a relative humidity of 10% to 90%. The crystalline form was sufficiently stable under long-term storage conditions (e.g., a temperature of 25° C. and a relative humidity of 60%) and accelerated conditions (e.g., a temperature of 40° C. and a relative humidity of 75%).

Example 5. Preparation of Methanesulfonate Monohydrate (Mesylate·1H$_2$O) of Compound of Formula 1

10 g (21.26 mmol) of the compound of Formula 1 was added to 100 mL of a 90% aqueous ethanol solution (ethanol/water=9/1). After adding dropwise 1.52 mL (23.38 mmol) of methane sulfonic acid to the reaction solution, the mixture was stirred at 20° C. to 25° C. for 12 hr. The precipitated solid was filtered. After washing the filtered product with 10 mL of ethanol and drying at 50° C., 10.9 g of the title compound (yield: 91.0%) was obtained.

Figure 1E:
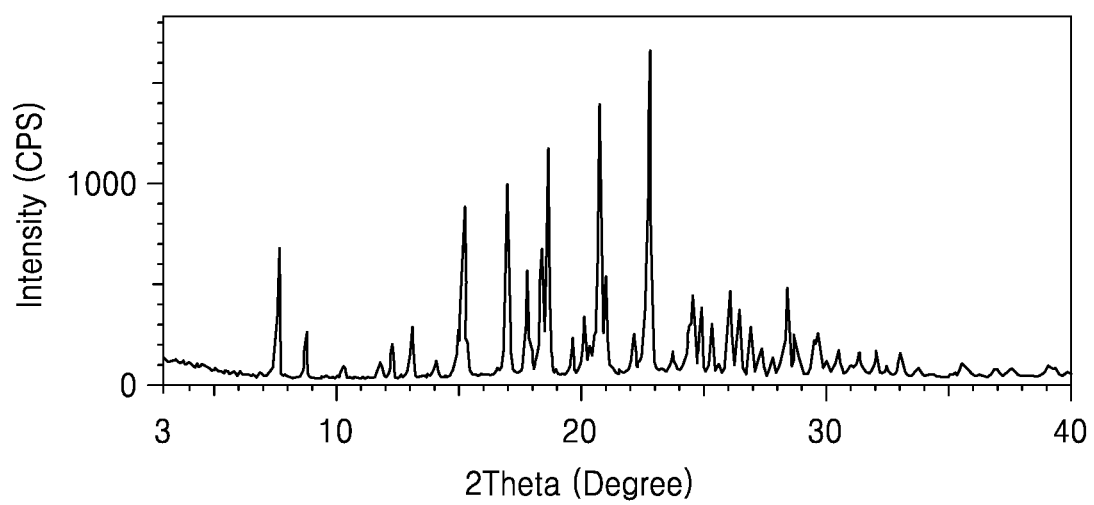
Figure 2E:
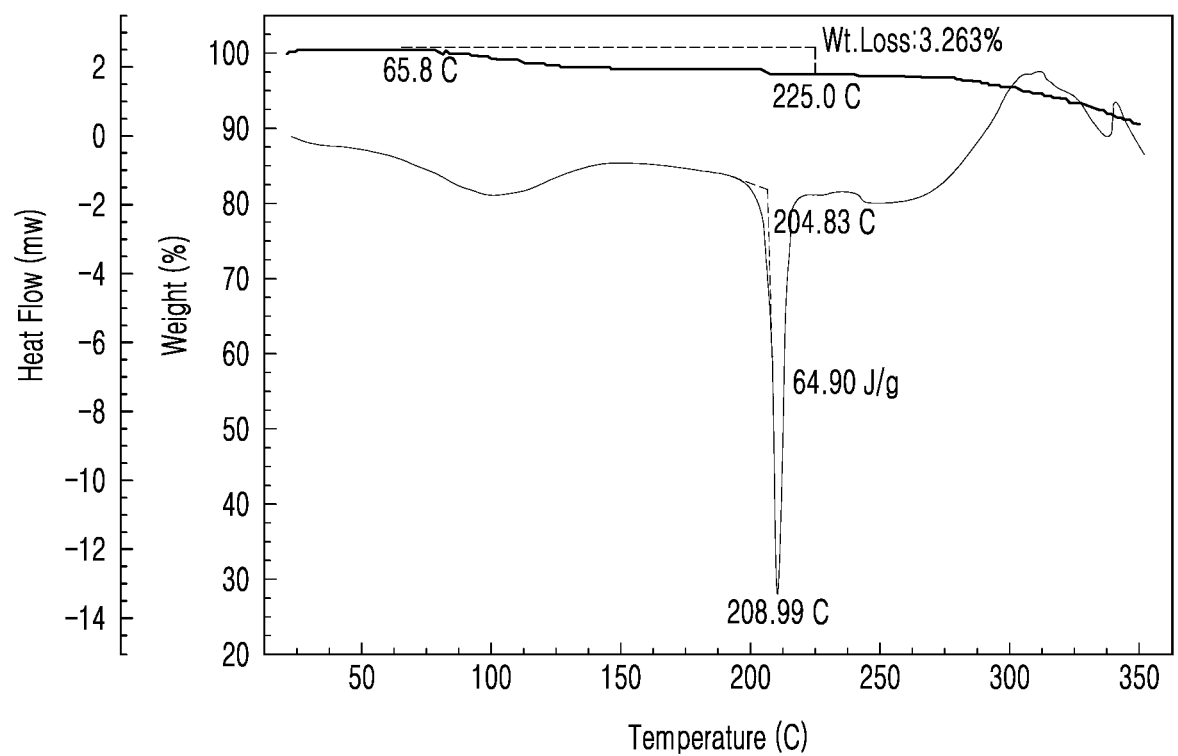
Figure 3E:
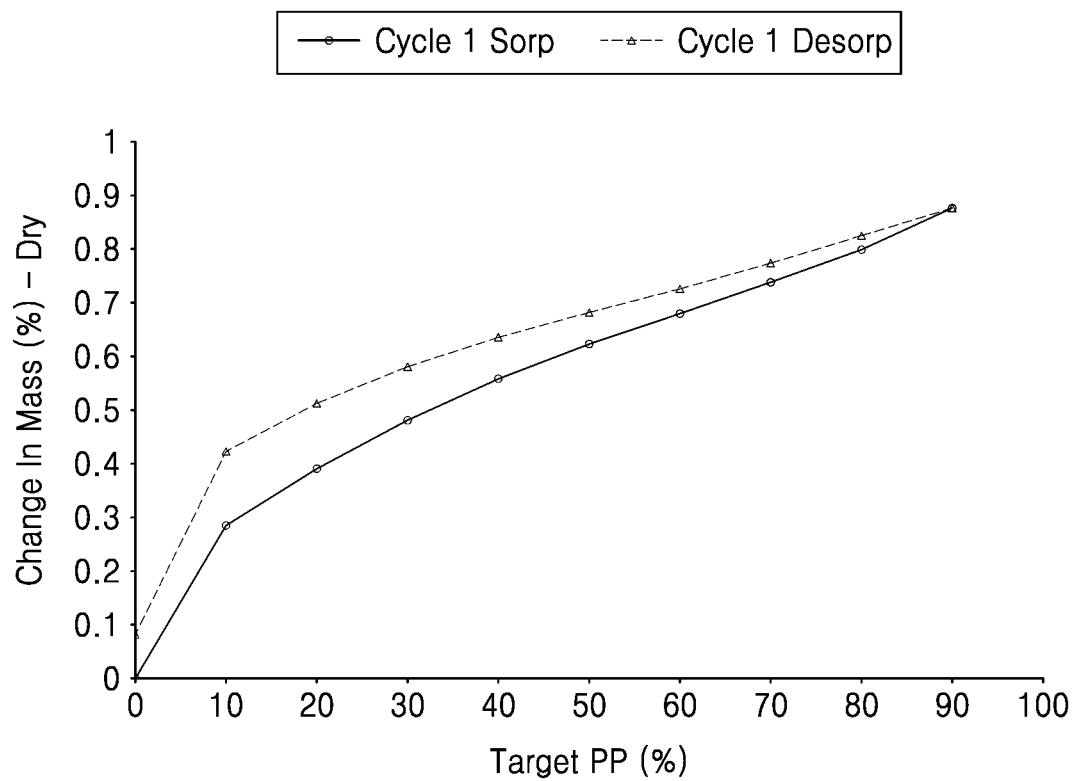

Water content: 3.1% (a theoretical value of monohydrate: 3.08%)
Analysis of Characteristics Results of XRPD, DSC, and DVS analyses of the crystalline form of methanesulfonate monohydrate (MsOH·1H$_2$O) of the compound of Formula 1 prepared in Example 5 are shown in FIGS. 1E, 2E, and 3E, respectively.

The peaks having a relative intensity ($I/I_o$) of 5% or higher in the XRPD spectrum of the above crystalline form are shown in Table 5 below. When the peaks had $I/I_0$ ratios equal to or higher than 10%, they appeared at diffraction angles (2θ±0.2°) of 7.6°, 8.8°, 12.3°, 13.1°, 14.9°, 15.2°, 17.0°, 17.8°, 18.4°, 18.7°, 19.7°, 20.1°, 20.8°, 21.0°, 22.1°, 22.8°, 24.6°, 24.9°, 25.4°, 26.1°, 26.5°, 27.0°, 27.4°, 28.4°, 28.8°, 29.7°, and 30.5°.

TABLE 5

| 2θ (±0.2) | d | $I/I_o$ (%) |
|---|---|---|
| 7.6 | 11.6 | 40.6 |
| 8.8 | 10.1 | 15.4 |
| 11.8 | 7.5 | 6.4 |
| 12.3 | 7.2 | 11.8 |
| 13.1 | 6.8 | 17 |

TABLE 5-continued

| 2θ (±0.2) | d | I/I$_o$ (%) |
|---|---|---|
| 14.1 | 6.3 | 7 |
| 14.9 | 5.9 | 14.2 |
| 15.2 | 5.8 | 52.9 |
| 17.0 | 5.2 | 59.6 |
| 17.8 | 5.0 | 34.3 |
| 18.4 | 4.8 | 40.4 |
| 18.7 | 4.8 | 70.4 |
| 19.7 | 4.5 | 12.3 |
| 20.1 | 4.4 | 19.8 |
| 20.8 | 4.3 | 83.7 |
| 21.0 | 4.2 | 32 |
| 22.1 | 4.0 | 15.1 |
| 22.8 | 3.9 | 100 |
| 23.7 | 3.7 | 9.8 |
| 24.6 | 3.6 | 26.8 |
| 24.9 | 3.6 | 23.2 |
| 25.4 | 3.5 | 18.3 |
| 26.1 | 3.4 | 27.8 |
| 26.5 | 3.4 | 19.8 |
| 27.0 | 3.3 | 17 |
| 27.4 | 3.3 | 10.4 |
| 27.9 | 3.2 | 7.3 |
| 28.4 | 3.1 | 29.2 |
| 28.8 | 3.1 | 14.5 |
| 29.7 | 3.0 | 14.6 |
| 30.0 | 3.0 | 6.5 |
| 30.5 | 2.9 | 10.8 |
| 31.0 | 2.9 | 5.6 |
| 31.3 | 2.9 | 9.8 |
| 32.1 | 2.8 | 9.7 |
| 32.5 | 2.8 | 5.3 |
| 33.1 | 2.7 | 9.2 |
| 35.6 | 2.5 | 6.1 |
| 37.6 | 2.4 | 5.3 |
| 39.2 | 2.3 | 5 |

2θ: diffraction angle, d: distance between crystal faces,
I/I$_o$ (%): relative intensity (I indicates the intensity of each peak; I$_o$ indicates the intensity of the highest peak)

The above crystalline form showed an endothermic peak at about 92.0° C. and an endothermic peak at about 209.0° C. in a DSC (10° C./min). In the DSC, the endothermic peak at about 92.0° C. indicates a dehydration point of the crystalline form of methanesulfonate monohydrate, and the endothermic peak at about 209.0° C. indicates a melting point.

The crystalline form showed a water content of about 3.1% (a theoretical water content of 3.08%) in a Karl-Fischer titrator and a melting point of about 204° C. to about 208° C.

In the DVS, the above crystalline form showed low water absorption of about 1% in the region with a relative humidity of 10% to 90%. The crystalline form was sufficiently stable under long-term storage conditions (e.g., a temperature of 25° C. and a relative humidity of 60%) and accelerated conditions (e.g., a temperature of 40° C. and a relative humidity of 75%).

Example 6. Preparation of Crystalline Form of Ethanesulfonic Anhydride (Esylate·Anhydrate) of Compound of Formula 1

Example 6.1. Preparation of Ethanol Anhydrous 10 g (21.26 mmol) of the compound of Formula 1 was added to 100 mL of ethanol. 1.92 mL (23.38 mmol) of ethanesulfonate was added dropwise to the reaction solution, followed by stirring at 20° C. to 25° C. for 3 hr. The precipitated solid was filtered. The filtered product was washed with 10 mL of ethanol and dried at 50° C. to obtain 10.5 g of the title compound (yield: 85.0%).

Water content: 0.3%

Example 6.2. Preparation in Aqueous Ethanol Solution 10 g (21.26 mmol) of the compound of Formula 1 was added to 100 mL of a 90% aqueous ethanol solution (ethanol/water=9/1). After adding dropwise 1.92 mL (23.38 mmol) of ethanesulfonate to the reaction solution, the mixture was stirred at 20° C. to 25° C. for 3 hr. The precipitated solid was filtered. After washing the filtered product with 10 mL of ethanol and drying at 50° C., 8.9 g of the title compound (yield: 73.0%) was obtained.

Water content: 0.2%

Analysis of Characteristics

Figure 1F:
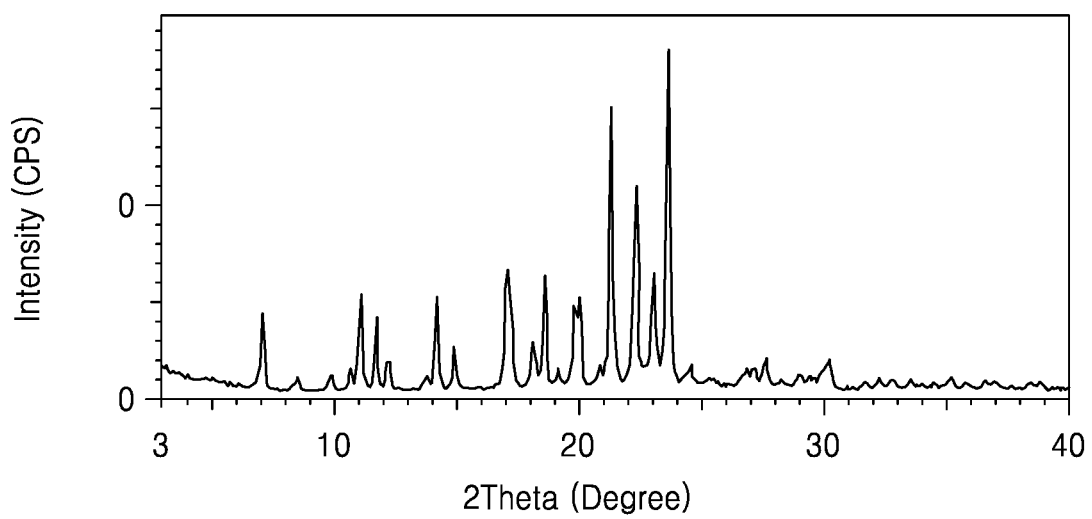
Figure 2F:
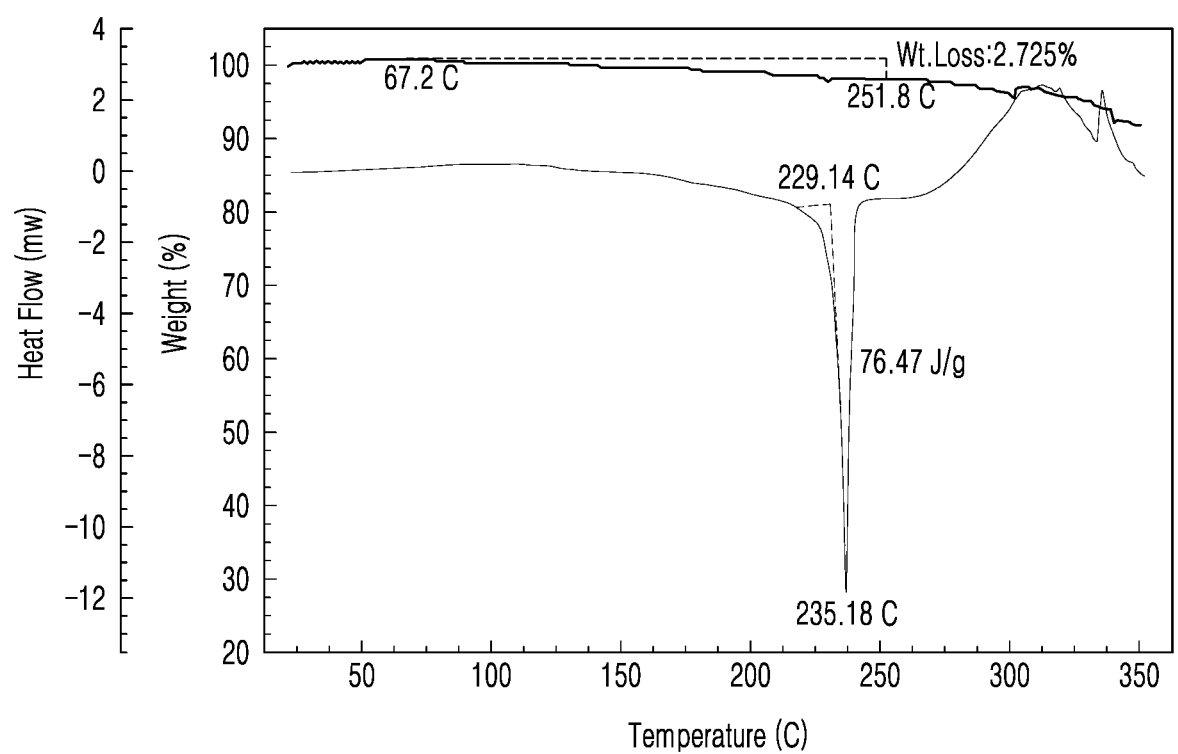
Figure 3F:
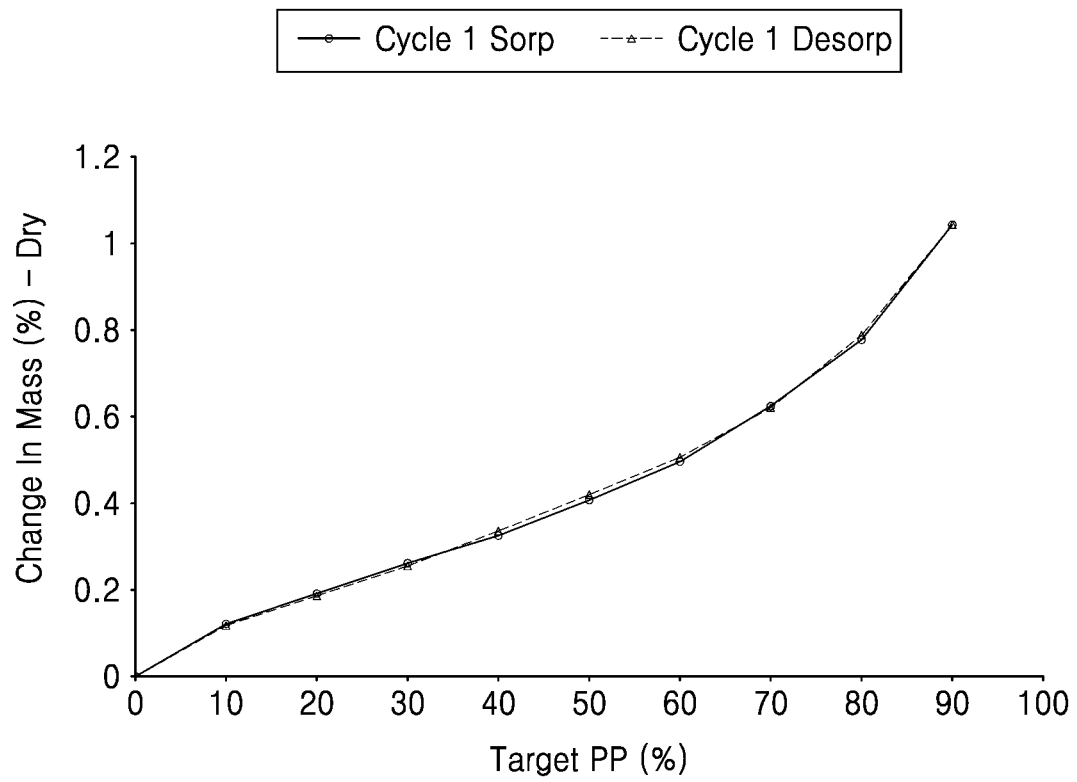

Results of XRPD, DSC, and DVS analyses of the crystalline form of ethanesulfonic anhydride (Esylate·anhydrate) of the compound of Formula 1 prepared in Example 6 are shown in FIGS. 1F, 2F, and 3F, respectively.

The peaks having a relative intensity (I/I$_o$) of 10% or higher in the XRPD spectrum of the above crystalline form are shown in Table 6 below. When the peaks had I/I$_o$ ratios equal to or higher than 10%, they appeared at diffraction angles (2θ±0.2°) of 7.1°, 11.1°, 11.7°, 12.2°, 14.2°, 14.9°, 17.1°, 18.1°, 18.6°, 19.8°, 20.0°, 21.3°, 22.3°, 23.0°, 23.6°, and 27.6°.

TABLE 6

| 2θ (±0.2) | d | I/I$_o$ (%) |
|---|---|---|
| 7.1 | 12.5 | 23.9 |
| 8.5 | 10.4 | 5.5 |
| 9.8 | 9.0 | 7.1 |
| 10.6 | 8.3 | 8.1 |
| 11.1 | 8.0 | 29.4 |
| 11.7 | 7.5 | 22.7 |
| 12.2 | 7.3 | 10.6 |
| 13.7 | 6.4 | 5.5 |
| 14.2 | 6.2 | 28.1 |
| 14.9 | 5.9 | 14.5 |
| 17.1 | 5.2 | 36.5 |
| 18.1 | 4.9 | 16.4 |
| 18.6 | 4.8 | 35.1 |
| 19.2 | 4.6 | 8.2 |
| 19.8 | 4.5 | 26.6 |
| 20.0 | 4.4 | 28.7 |
| 20.8 | 4.3 | 9.5 |
| 21.3 | 4.2 | 83.4 |
| 22.3 | 4.0 | 60.9 |
| 23.0 | 3.9 | 35.7 |
| 23.6 | 3.8 | 100 |
| 24.5 | 3.6 | 9.2 |
| 26.9 | 3.3 | 7.7 |
| 27.2 | 3.3 | 8.1 |
| 27.6 | 3.2 | 11.2 |
| 28.3 | 3.2 | 5 |
| 29.0 | 3.1 | 6.5 |
| 30.2 | 3.0 | 9.3 |
| 32.3 | 2.8 | 5.4 |
| 32.8 | 2.7 | 5 |
| 35.2 | 2.5 | 5.6 |

2θ: diffraction angle, d: distance between crystal faces,
I/I$_o$ (%): relative intensity (I indicates the intensity of each peak; I$_o$ indicates the intensity of the highest peak)

The above crystalline form showed an endothermic peak at about 235.2° C. in a DSC (10° C./min). In the DSC, the endothermic peak at about 235.2° C. indicates a melting point.

The crystalline form showed a water content of about 0.3% in a Karl-Fischer titrator and a melting point of about 229° C. to about 235° C.

In the DVS, the above crystalline form showed low water absorption of about 1% in the region with a relative humidity of 10% to 90%. The crystalline form was sufficiently stable under long-term storage conditions (e.g., a temperature of 25° C. and a relative humidity of 60%) and accelerated conditions (e.g., a temperature of 40° C. and a relative humidity of 75%).

Experimental Example 1. Measurement of Water Solubility

To measure water solubility, each sample of the acid addition salts of the compound of Formula 1 prepared in Examples 1 to 6 was prepared in deionized water under the following conditions, and then each solution was analyzed by HPLC according to content measurement conditions of the compound of Formula 1. The dissolved amounts (LOD: more than 0.001 mg/mL) based on the compound of Formula 1 were measured, and then the values were converted. The resulting values are shown in Tables 7 and 8 below.

In detail, each 100 mg of various forms was added to 5 mL of water, and mixed using a Voltamixer at 20° C. to 25° C., and a filtrate filtered using GH Polypro membrane Acrodisc, PALL (pore size of 0.2 μm) was diluted with a dilution solvent for HPLC.

TABLE 7

| Acid addition salt | Formula 1 (Free base) | 2HCl·3H$_2$O | 1HCl·2H$_2$O | 1HCl·anhydrous |
|---|---|---|---|---|
| Concentration of solution (mg/mL) | 20 | 20 | 20 | 20 |
| Solubility (mg/mL) | 0.001 | 0.9~1.4 | 0.3~0.7 | 1.27 |
| pH of solution | 7.2~7.3 | 2.3~2.4 | 5.8~5.9 | 5.9~6.0 |

TABLE 8

| Acid addition salt | Formula 1 (Free base) | 1MsOH·anhydrous | 1MsOH·1H$_2$O | 1EsOH anhydrous |
|---|---|---|---|---|
| Concentration of solution (mg/mL) | 20 | 20 | 20 | 20 |
| Solubility (mg/mL) | 0.001 | 1.13 | 0.93 | 9.59 |
| pH of solution | 7.2~7.3 | 6.3 | 6.1 | 6.3 |

As shown in Table 7, solubility of hydrochloride of the compound of Formula 1 was high, as compared with that of the compound of Formula 1 (free base), and in particular, dihydrochloride of the compound of Formula 1 showed higher solubility than the crystalline form of the monohydrochloride.

Among the hydrochlorides of the compound of Formula 1, the crystalline form of dihydrochloride trihydrate is expected to be the most beneficial in terms of a pharmaceutical composition, considering dissolution, etc.

Further, as shown in Table 8, solubility of sulfonate of the compound of Formula 1 was remarkably high, as compared with that of the compound of Formula 1 (free base), and in particular, the crystalline form of ethanesulfonic anhydride of the compound of Formula 1 showed remarkably high solubility.

Therefore, among the sulfonates of the compound of Formula 1, the crystalline form of ethanesulfonic anhydride is expected to be the most beneficial in terms of a pharmaceutical composition, considering dissolution, etc.

The invention claimed is:

1. A crystalline form of an acid addition salt of the following compound of Formula 1:

[Formula 1]

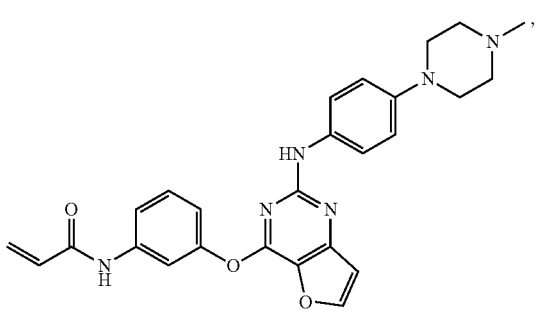

wherein the crystalline form is selected from:

a crystalline form of dihydrochloride trihydrate (2HCl·3H$_2$O) of the compound of Formula 1 and has an X-ray powder diffraction (XRPD) spectrum comprising peaks at diffraction angles (2θ±0.2°) of 6.4°, 7.1°, 12.8°, 15.6°, and 21.2°, when irradiated with a Cu-Kα light source;

a crystalline form of monohydrochloride dihydrate (1HCl·2H$_2$O) of the compound of Formula 1 and has an X-ray powder diffraction (XRPD) spectrum comprising peaks at diffraction angles (2θ±0.2°) of 7.0°, 7.9°, 15.8°, 17.2°, 18.6°, 20.6°, 21.3°, and 23.2°, when irradiated with a Cu-Kα light source;

a crystalline form of monohydrochloride anhydrous (1HCl) of the compound of Formula 1 and has an X-ray powder diffraction (XRPD) spectrum comprising peaks at diffraction angles (2θ±0.2°) of 4.9°, 14.8°, and 21.2°, when irradiated with a Cu-Kα light source;

a crystalline form of methanesulfonic anhydride (1MsOH) of the compound of Formula 1 and has an X-ray powder diffraction (XRPD) spectrum comprising peaks at diffraction angles (2θ±0.2°) of 11.8°, 17.2°, 19.0°, 20.0°, 22.8°, and 24.0°, when irradiated with a Cu-Kα light source;

a crystalline form of methanesulfonate monohydrate (1MsOH·1H$_2$O) of the compound of Formula 1 and has an X-ray powder diffraction (XRPD) spectrum comprising peaks at diffraction angles (2θ±0.2°) of 7.6°, 15.2°, 17.0°, 18.7°, 20.8°, and 22.8°, when irradiated with a Cu-Kα light source; or a crystalline form of ethanesulfonic anhydride (1EsOH) of the compound of Formula 1 and has an X-ray powder diffraction (XRPD) spectrum comprising peaks at diffraction angles (2θ+0.2°) of 17.1°, 18.6°, 21.3°, 22.3°, 23.0°, and 23.6°, when irradiated with a Cu-Kα light source.

2. A pharmaceutical composition comprising a crystalline form of an acid addition salt of the following compound of Formula 1:

[Formula 1]

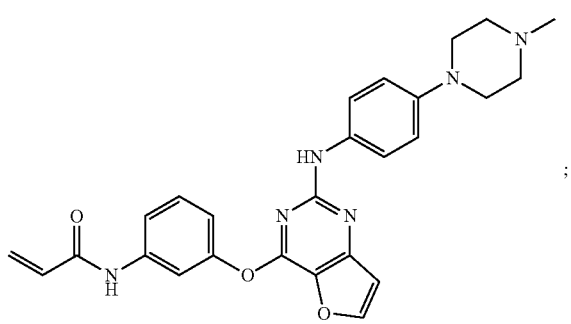

and one or more pharmaceutically acceptable carriers or diluents,
wherein the crystalline form is selected from:
a crystalline form of dihydrochloride trihydrate (2HCl·3H$_2$O) of the compound of Formula 1 and has an X-ray powder diffraction (XRPD) spectrum comprising peaks at diffraction angles (2θ-0.2°) of 6.4°, 7.1°, 12.8°, 15.6°, and 21.2°, when irradiated with a Cu-Kα light source;
a crystalline form of monohydrochloride dihydrate (1HCl·2H$_2$O) of the compound of Formula 1 and has an X-ray powder diffraction (XRPD) spectrum comprising peaks at diffraction angles (2θ-0.2°) of 7.0°, 7.9°, 15.8°, 17.2° 18.6°, 20.6°, 21.3°, and 23.2°, when irradiated with a Cu-Kα light source;
a crystalline form of monohydrochloride anhydrous (1HCl) of the compound of Formula 1 and has an X-ray powder diffraction (XRPD) spectrum comprising peaks at diffraction angles (2θ-0.2°) of 4.9°, 14.8°, and 21.2°, when irradiated with a Cu-Kα light source;
a crystalline form of methanesulfonic anhydride (1MsOH) of the compound of Formula 1 and has an X-ray powder diffraction (XRPD) spectrum comprising peaks at diffraction angles (2θ-0.2°) of 11.8°, 17.2°, 19.0°, 20.0°, 22.8°, and 24.0°, when irradiated with a Cu-Kα light source;
a crystalline form of methanesulfonate monohydrate (1MsOH·1H$_2$O) of the compound of Formula 1 and has an X-ray powder diffraction (XRPD) spectrum comprising peaks at diffraction angles (2θ±0.2°) of 7.6°, 15.2°, 17.0°, 18.7°, 20.8°, and 22.8°, when irradiated with a Cu-Kα light source;
a crystalline form of ethanesulfonic anhydride (1EsOH) of the compound of Formula 1 and has an X-ray powder diffraction (XRPD) spectrum comprising peaks at diffraction angles (2θ+0.2°) of 17.1°, 18.6°, 21.3°, 22.3°, 23.0°, and 23.6°, when irradiated with a Cu-Kα light source; or
a combination thereof.

3. The pharmaceutical composition of claim 2, wherein the pharmaceutical composition is used for treating a benign or malignant tumor, an inflammatory disease, or an autoimmune disease, which are caused by epithelial growth factor receptor tyrosine kinase or a variant thereof.

4. A method for treating an epithelial growth factor receptor tyrosine kinase-mediated disease in a subject in need thereof, comprising administering the pharmaceutical composition of claim 2 to the subject, wherein the epithelial growth factor receptor tyrosine kinase-mediated disease is a benign or malignant tumor, an inflammatory disease, or an autoimmune disease.

5. The pharmaceutical composition of claim 3, wherein the autoimmune disease is rheumatoid arthritis.

* * * * *